US010300027B2

(12) United States Patent
Levis et al.

(10) Patent No.: US 10,300,027 B2
(45) Date of Patent: May 28, 2019

(54) EFFECTIVE SENSITIZING DOSE OF A GELLED IMMUNOMODULATING TOPICAL COMPOSITION

(71) Applicant: Phio Pharmaceuticals Corp., Marlborough, MA (US)

(72) Inventors: William R. Levis, New York, NY (US); Leonard L. Kaplan, East Brunswick, NJ (US); John G. Callahan, Moorestown, NJ (US)

(73) Assignee: Phio Pharmaceuticals Corp., Marlborough, MA (US)

( * ) Notice: Subject to any disclaimer, the term of this patent is extended or adjusted under 35 U.S.C. 154(b) by 0 days.

(21) Appl. No.: 14/532,694

(22) Filed: Nov. 4, 2014

(65) Prior Publication Data

US 2015/0057362 A1 Feb. 26, 2015

Related U.S. Application Data

(63) Continuation of application No. 13/035,692, filed on Feb. 25, 2011, now abandoned.

(60) Provisional application No. 61/309,717, filed on Mar. 2, 2010.

(51) Int. Cl.
| | | |
|---|---|---|
| *A61K 39/12* | (2006.01) |
| *A61K 31/122* | (2006.01) |
| *A61K 9/00* | (2006.01) |
| *A61K 47/10* | (2017.01) |
| *A61K 47/14* | (2017.01) |
| *A61K 47/26* | (2006.01) |
| *A61K 9/06* | (2006.01) |

(52) U.S. Cl.
CPC .......... *A61K 31/122* (2013.01); *A61K 9/0014* (2013.01); *A61K 9/06* (2013.01); *A61K 47/10* (2013.01); *A61K 47/14* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 4,020,183 A | 4/1977 | Asculai et al. |
| 4,985,464 A | 1/1991 | Happle et al. |
| 4,997,851 A | 3/1991 | Isaacs et al. |
| 6,455,586 B1 | 9/2002 | Kaplan et al. |
| 6,761,900 B2 | 7/2004 | Shudo et al. |
| 7,067,254 B2 | 6/2006 | Kumamoto et al. |
| 7,838,564 B2 | 11/2010 | Alonso et al. |
| 8,664,189 B2 | 3/2014 | Khvorova et al. |
| 8,796,443 B2 | 8/2014 | Khvorova et al. |
| 8,815,818 B2 | 8/2014 | Samarsky et al. |
| 9,074,211 B2 | 7/2015 | Woolf et al. |
| 9,080,171 B2 | 7/2015 | Khvorova et al. |
| 9,095,504 B2 | 8/2015 | Libertine et al. |
| 9,175,289 B2 | 11/2015 | Khvorova et al. |
| 9,303,259 B2 | 4/2016 | Khvorova et al. |
| 9,340,786 B2 | 5/2016 | Khvorova et al. |
| 9,493,774 B2 | 11/2016 | Kamens |
| 9,745,574 B2 | 8/2017 | Woolf et al. |
| 9,938,530 B2 | 4/2018 | Khvorova et al. |
| 9,963,702 B2 | 5/2018 | Khvorova et al. |
| 10,041,073 B2 | 8/2018 | Khvorova et al. |
| 10,131,904 B2 | 11/2018 | Pavco et al. |
| 10,138,485 B2 | 11/2018 | Khvorova et al. |
| 2002/0128326 A1* | 9/2002 | Kaplan ................ A61K 9/0014 514/763 |
| 2005/0201959 A1 | 9/2005 | David |
| 2005/0260136 A1 | 11/2005 | Kaplan et al. |
| 2006/0211766 A1 | 9/2006 | Kaplan et al. |
| 2006/0211866 A1 | 9/2006 | Joshi et al. |
| 2008/0044444 A1 | 2/2008 | Tamarkin et al. |
| 2009/0131360 A1 | 5/2009 | Woolf et al. |
| 2010/0041767 A1 | 2/2010 | Carter et al. |
| 2010/0069620 A1 | 3/2010 | Zon |
| 2011/0251258 A1 | 10/2011 | Samarsky et al. |
| 2011/0268761 A1 | 11/2011 | Levis et al. |
| 2013/0136700 A1 | 5/2013 | Davey et al. |
| 2014/0037695 A1 | 2/2014 | Yu et al. |
| 2014/0065153 A1 | 3/2014 | Christiano et al. |
| 2014/0242012 A1 | 8/2014 | Cozzi et al. |
| 2014/0274982 A1 | 9/2014 | Bakan et al. |
| 2016/0115482 A1 | 4/2016 | Libertine et al. |
| 2016/0115484 A1 | 4/2016 | Woolf et al. |
| 2016/0130578 A1 | 5/2016 | Khvorova et al. |

(Continued)

FOREIGN PATENT DOCUMENTS

| | | |
|---|---|---|
| WO | WO 96/32142 A1 | 10/1996 |
| WO | WO 2010/011346 A2 | 1/2010 |

(Continued)

OTHER PUBLICATIONS

Damian and Thompson. Treatment of extensive cutaneous metastatic melanoma with topical diphencyprone. J. Am. Acad. Dermatol. 2007; 56(5) 869-871.*
Buckley and du Vivier. The therapeutic use of topical contact sensitizers in benign dermatoses. Br. J. Dermatol. 2001; 145: 385-405.*
http://www.quit.org.au/about/frequently-asked-questions/faq-nicotine-patches/faq-nicotine-patches-side-effects.html—downloaded May 2, 2016.*
Handisurya et al. Diseases caused by human papillomaviruses (HPV), J. German Soc. Dermatol. 2009; 7:453-466.*
Hengge et al. "Topical immunomodulators—progress towards treating inflammation, infection, and cancer", Lancet: Inf. Diseas. 2001; 1: 189-198.*
Kirnbauer R, Hubbert NL, Wheeler CM, Becker TM, Lowy DR, Schiller JT. A virus-like particle enzyme-linked immunosorbent assay detects serum antibodies in a majority of women infected with human papillomavirus type 16. J Natl Cancer Inst. 1994; 86(7): 494-9.*

(Continued)

*Primary Examiner* — Janet L Andres
*Assistant Examiner* — Stuart W Snyder
(74) *Attorney, Agent, or Firm* — Wolf, Greenfield & Sacks, P.C.

(57) ABSTRACT

The present invention relates to compositions and methods of treating warts and other human papilloma virus (HPV) skin infections. The present invention relates to compositions and methods of treating skin cancer.

12 Claims, No Drawings

(56) References Cited

U.S. PATENT DOCUMENTS

| | | | |
|---|---|---|---|
| 2016/0244765 | A1 | 8/2016 | Khvorova et al. |
| 2016/0304873 | A1 | 10/2016 | Wolfson et al. |
| 2016/0304875 | A1 | 10/2016 | Cauwenbergh et al. |
| 2017/0009239 | A1 | 1/2017 | Khvorova et al. |
| 2017/0051288 | A1 | 2/2017 | Byrne et al. |
| 2017/0051290 | A1 | 2/2017 | Byrne et al. |
| 2017/0137823 | A1 | 5/2017 | Kamens et al. |
| 2018/0030451 | A1 | 2/2018 | Cauwenbergh |
| 2018/0155718 | A1 | 6/2018 | Woolf et al. |
| 2018/0195066 | A1 | 7/2018 | Byrne et al. |
| 2018/0195072 | A1 | 7/2018 | Cardia et al. |
| 2018/0263925 | A1 | 9/2018 | Cauwenbergh et al. |
| 2018/0327748 | A1 | 11/2018 | Khvorova et al. |

FOREIGN PATENT DOCUMENTS

| | | |
|---|---|---|
| WO | WO 2010/033246 A1 | 3/2010 |
| WO | WO 2011/119887 A1 | 9/2011 |
| WO | WO 2016/090173 A1 | 6/2016 |

OTHER PUBLICATIONS

FDA, NDA 20-165/S-024, 2006 (see copyright to GlaxoSmithKline Consumer Healthcare, L.P. for NicoDerm CQ).*

Buckley et al., "The therapeutic use of topical contact sensitizers in benign dermatoses." 2001 Br J Dermatol 145(3):385-405.

Damian et al., "Topical diphencyprone immunotherapy for cutaneous metastic melanoma." 2009 Australas J Dermatol 50:266-71.

Ferry et al., "Immunotherapy with dinitrochlorobenzene (DNCB) for recurrent squamous cell tumor conjunctiva." 1976, Trans Am Ophthalmol Soc 74:154-71.

Levis et al., "Topical Diphenylcyclopropenone as a measure of immune competence in HIV-Seropostive subjects." 2006, J Drugs Dermatol. 5(9):853-8.

Levis et al., "Topical Immunotherapy of Basal Cell Carcinmomas with Dinitrochlorobenzene." 1973, Cancer Res 33(11):3036-3042.

Mangana et al., "Prevalance of Merkel Cell Polyomavirus among Swiss Merkel Cell Carcinoma Patients." 2010, Dermatology 221:184-188.

Olsen et al., "Sezary syndrome: Immunopathogenesis, literature review of therapeutic options, and recommendations for therapy by the United Staets Cutaneous Lymphoma Consortium (USCLC)." 2011, J Am Acad Dermatol 64(2):352-404.

Paulino, "A randomized, double blinded, vehicle controlled study of Topical Diphenlcyclopropenone contact Immunotherapy for the treatment of Verruca Warts conditions—Summarhy of clinician/patient reported adverse effects." 2010 Instituto Dominicano de Estudios Virologicos—IDEV, Sando Domingo, DR. pp. 1-15.

Raaf et al., "Treatment of Bowen's Disease with Topical Dinitrochlorobenzene and 5-Flourouracil." 1976, Cancer 37(4):1633-1642.

Samarasinghe et al., "Focus on basal Cell Cardinoma." 2011, J Skin Cancer 2011:328615.

Upitis and Krol, "The use of diphenylcyclopropenone in the treatment of recalcitrant warts." 2002 J Cutaneous Med Surg 6(3):214-217.

Von Nida and Quirk, "Successful treatment of in-transit melanoma metastases using topica 2-4-dinitrochlorobenzene." 2003, Australas J Dermatol 44(4):277-280.

Vonderheid et al., "The prognostic significance of delayed hypersensitivity to dinitrochlorobenzene and mechlorethamine hydrochloride in cutaneous T cell lymphoma." 1998, J Invest Dermatol 110(6):946-950.

Extended European Search Report dated Jun. 4, 2014 in connection with EP 11751116.2.

International Search Report and Written Opinion dated May 9, 2011 in connection with PCT/US2011/26310.

International Preliminary Report on Patentability dated Sep. 13, 2012 in connection wth PCT/US2011/26310.

[No Author Listed] Merck Index, 10th edition, Windholz et al ED., Merck, Dohm & Sharp, Rahway, NJ, abstract #7455. 1984.

[No Author Listed] Current Therapy—Adjuvant Treatment of Melanoma. Northern California Melanoma Center. 2008. <http://www.melanomacenter.com/whatis/mealanoma_therapy_adj.html> Last accessed Sep. 10, 2009.

CAPLUS Chemical Abstracts Service Accession No. 1998:435434, DN129: 130918. (Loftsson et al., Fatty acid extract from cod-liver oil: activity against herpes simplex virus and enhancement of transdermal delivery of acyclovir in-vitro Pharm. Pharmacol Commun. 1998;4(6):287-291.).

CAPLUS Chemical Abstracts Service Accession No. 1983:581485, DN99:181485. (EP Patent 0 087 161, A2, published Aug. 31, 1983).

Balch et al., Final version of 2009 AJCC melanoma staging and classification. J Clin Oncol. Dec. 20, 2009;27(36):6199-206. Doi: 10.1200/JCO.2009.23.4799. Epub Nov. 16, 2009.

Baykal et al., Chapter 16: Cutaneous Metastasis. *Clinical Atlas of Skin Tumors*. Jan. 10, 2014: 467-76.

Bichakjian et al., Guidelines of care for the management of primary cutaneous melanoma. American Academy of Dermatology. J Am Acad Dermatol. Nov. 2011;65(5):1032-47. Doi: 10.1016/j.jaad.2011.04.031. Epub Aug. 25, 2011.

Dunki-Jacobs et al., Current management of melanoma. Curr Probl Surg. Aug. 2013;50(8):351-82. Doi: 10.1067/j.cpsurg.2013.04.001.

Evans et al., Birth incidence and prevalence of tumor-prone syndromes: estimates from a UK family genetic register service. Am J Med Genet A. Feb. 2010;152A(2):327-32. Doi: 10.1002/ajmg.A.33139.

Gulati, Treatment of cutaneous metastases with diphenylcyclopropenone (DPCP). Clinical Trial No. NCT01711684. Oct. 18, 2012. Retrieved online via https://clinicaltrials.gov/ct2/show/study/NCT01711684. Last accessed Feb. 25, 2016. 3 pages.

Hahn et al., Mutations of the human homolog of *Drosophila* patched in the nevoid basal cell carcinoma syndrome. Cell. Jun. 14, 1996;85(6):841-51.

Herrmann et al., "Complete remission of Merkel cell carcinoma of the scalp with local and regional metastases after topical treatment with dinitrochlorbenzol." 2004, J Am Acad Dermatol 50(6):965-969.

Johnson et al., Human homolog of patched, a candidate gene for the basal cell nevus syndrome. Science. Jun. 14, 1996;272(5268):1668-71.

Klein, Hypersensitivity reactions at tumor sites. Cancer Res. Dec. 1969;29(12):2351-62.

Leiter et al., The natural course of cutaneous melanoma. J Surg Oncol. Jul. 1, 2004;86(4):172-8.

Levis, Lymphokine production in cell-mediated allergic contact dermatitis. Lancet. Aug. 18, 1973;2(7825):389-90.

Mirvish et al., Infectious agents in cutaneous T-cell lymphoma. J Am Acad Dermatol. Feb. 2011;64(2):423-31. Doi: 10.1016/j.jaad.2009.11.692. Epub Aug. 7, 2010.

Muranski et al., Tumor-specific Th17-polarized cells eradicate large established melanoma. Blood. Jul. 15, 2008;112(2):362-73. Doi: 10.1182/blood-2007-11-120998. Epub Mar. 19, 2008.

Naylor et al., Contact immunotherapy of resistant warts. J Am Acad Dermatol. Oct. 1988;19(4):679-83.

Ott et al., Treatment for advanced melanoma: new drugs, new opportunities, new challenges. Oncology (Williston Park). May 2013;27(5):381-92, 391.

Rhee et al., Proper Concentration of Diphenylcyclopropenone Solution according to the Anatomical Location and Application Time Interval for the Treatment of Warts. Korean J. Dermatol. May 2009;47(5):524-30.

Stjernsward, Delayed hypersensitivity-induced regression of human neoplasms. Cancer. Sep 1971;28(3):628-40.

Stricker et al., Improved results of delayed-type hypersensitivity skin testing in HIV-infected patients treated with topical dinitrochlorobenzene. J Am Acad Dermatol. Oct. 1995;33(4):608-11.

Stricker et al., Comments: J Amer Acad Derm. Sep. 1996;35:492-3.

Stricker et al., Topical Immunomodulation; a Novel Approach to Immunotherapy. Immuno Letters. Dec. 1997;59:145-50.

(56) References Cited

OTHER PUBLICATIONS

Takeuchi et al., Sentinel lymph node as a target of molecular diagnosis of lymphatic micrometastasis and local immunoresponse to malignant cells. Cancer Sci. Mar. 2008;99(3):441-50.
Von Euw et al., CTLA4 blockade increases Th17 cells in patients with metastatic melanoma. J Transl Med. May 20, 2009;7:35. doi: 10.1186/1479-5876-7-35.
Wei et al., microRNAs: critical regulators in Th17 cells and players in diseases. Cell Mol Immunol. May 2010;7(3):175-81. doi: 10.1038/cmi.2010.19. Epub Apr. 5, 2010.
Rancan et al., Utilization of biodegradable polymeric materials as delivery agents in dermatology. Clin Cosmet Investig Dermatol. Jan. 9, 2014;7:23-34. doi: 10.2147/CCID.S39559. eCollection 2014.
Acosta-Rodriguez et al., Interleukins 1beta and 6 but not transforming growth factor-beta are essential for the differentiation of interleukin 17-producing human T helper cells. Nat Immunol. Sep. 2007;8(9):942-9. Epub Aug. 5, 2007.
Asai et al., A novel telomerase template antagonist (GRN163) as a potential anticancer agent. Cancer Res. Jul. 15, 2003;63(14):3931-9.
Baker et al., Therapeutic approaches to papillomavirus infections. Dermatol Clin. Apr. 1997;15(2):331-40. Review.
Barth et al., Interferon gamma and tumor necrosis factor have a role in tumor regressions mediated by murine CD8+ tumor-infiltrating lymphocytes. J Exp Med. Mar. 1, 1991;173(3):647-58.
Beaudenon et al., A novel type of human papillomavirus associated with genital neoplasias. Nature. May 15-21, 1986;321(6067):246-9.
Chen et al., Th17 cells: a new fate for differentiating helper T cells. Immunol Res. 2008;41(2):87-102. doi: 10.1007/s12026-007-8014-9. Review.
Damm et al., A highly selective telomerase inhibitor limiting human cancer cell proliferation. EMBO J. Dec. 17, 2001;20(24):6958-68.
Frazer, The role of vaccines in the control of STDs: HPV vaccines. Genitourin Med. Dec. 1996;72(6):398-403. Review.
Freyschmidt-Paul et al., Alopecia areata: treatment of today and tomorrow. J Investig Dermatol Symp Proc. Jun. 2003;8(1):12-7. Review.
Holloway et al., Identification of human papillomavirus type 16 in primary and recurrent cervical cancer following radiation therapy. Gynecol Oncol. May 1991;41(2):123-8.
Houghton et al., Immunity against cancer: lessons learned from melanoma. Curr Opin Immunol. Apr. 2001;13(2):134-40. Review.
Leong, Immunotherapy of malignant melanoma. Surg Clin North Am. Dec. 1996;76(6):1355-81. Review.
Lorincz et al., Human papillomavirus infection of the cervix: relative risk associations of 15 common anogenital types. Obstet Gynecol. Mar. 1992;79(3):328-37.
Ramirez et al., Topical imiquimod as an adjuvant to laser removal of mature tattoos in an animal model. Dermatol Surg. Mar. 2007;33(3):319-25.
Rosenberg et al., A new approach to the adoptive immunotherapy of cancer with tumor-infiltrating lymphocytes. Science. Sep. 19, 1986;233(4770):1318-21.
Rosenberg et al., Karnofsky Memorial Lecture. The immunotherapy and gene therapy of cancer. J Clin Oncol. Feb. 1992;10(2):180-99. Review.
Rosenberg et al., Use of tumor-infiltrating lymphocytes and interleukin-2 in the immunotherapy of patients with metastatic melanoma. A preliminary report. N Engl J Med. Dec. 22, 1988;319(25):1676-80.
Skorski et al., Antileukemia effect of c-myc N3'-->P5' phosphoramidate antisense oligonucleotides in vivo. Proc Natl Acad Sci U S A. Apr. 15, 1997;94(8):3966-71.
Solis et al., Experimental Nonsurgical Tattoo Removal in a Guinea Pig Model with Topical Imiquimod and Tretinoin. 2002;28:83-7.
Van Driei et al., the current status of therapeutic HPV vaccine. Ann Med. Dec. 1996;28(6):471-7. Review.
Wilson et al., Development, cytokine profile and function of human interleukin 17-producing helper T cells. Nat Immunol. Sep. 2007;8(9):950-7.
Wolchok et al., Vaccines for melanoma: translating basic immunology into new therapies. Lancet Oncol. Apr. 2001;2(4):205-11. Review.
Yang et al., IL-21 and TGF-beta are required for differentiation of human T(H)17 cells. Nature. Jul. 17, 2008;454(7202):350-2. doi: 10.1038/nature07021. Epub May 11, 2008.
Zur Hausen, Papillomaviruses causing cancer: evasion from host-cell control in early events in carcinogenesis. J Natl Cancer Inst. May 3, 2000;92(9):690-8. Review.

\* cited by examiner

EFFECTIVE SENSITIZING DOSE OF A GELLED IMMUNOMODULATING TOPICAL COMPOSITION

CROSS-REFERENCE TO RELATED APPLICATIONS

The present application is a continuation of, and claims priority to, U.S. patent application Ser. No. 13/035,692, filed Feb. 25, 2011, which claims priority under 35 U.S.C. § 119(e) to U.S. Provisional Patent Application No. 61/309,717, filed Mar. 2, 2010, all of which applications are incorporated herein by reference in their entireties.

BACKGROUND OF THE INVENTION

Human papilloma virus (HPV) is a small double-stranded DNA virus that colonizes various stratified epithelia like skin, oral and genital mucosa, and induces the formation of self-limiting benign tumors known as papillomas (warts) or condylomas. Most of these benign tumors naturally regress due to the influence of host immunological defenses. Some HPVs, however, have oncogenic potential and have been associated with certain types of cancers, See, Lorincz et al., Obstetrics & Gynecology, 79:328-337 (1992); Beaudenon et al., Nature, 321:246-249 (1986); and Holloway et al., Gynecol, One., 41:123-128 (1991).

Infection with HPV is common. HPV can be transmitted sexually, and it is estimated that 20-80% of sexually active adults have been infected. While a majority of infections are asymptomatic, infection can lead to the development of genital warts (which have a prevalence of about 1-5% among adults) and cancer of the anogenital tract. Another type of cancer, cervical cancer, is strongly associated with HPV (Frazer, Genitourin. Med. 72:398-403, 1996), HPV types 6, 11, 16, 18, 31, and 33 are often associated with an increased risk of cancer, with types 16 and/or 18 being detected in more than 90% of cervical carcinomas (van Driel et al., Ann. Med. 28:471-477, 1996). Types 6 and 11 are also associated with anogenital warts. For reviews of papilloma viruses and their associated pathologies, see Shah et al., "Chapter 66: Papillomaviruses," In: Virology, 3rd Edition, Fields et al., Eds., Raven Press, Philadelphia, pp 2077-2109, 1996, and zur Hansen, J. Natl, Cancer Inst. 92:690-698, 2000.

Verrucae or human warts are benign epidermal tumors caused by human papilloma virus HPV. HPV is a member of the papovavirus family. HPV is a non-enveloped double-stranded deoxyribonucleic acid (DNA) virus that replicates in epithelial cells. This means that HPV has a predilection for the mucosa and skin. Currently, there are more than 70 distinct HPV types recognized each with at least a 10% genome difference. Because papillomaviruses tend to be host-specific and HPV has not been successfully grown in culture; the majority of the research with papilloma virus has been conducted with animal papillomaviruses. Papillomaviruses are considered responsible for several forms of viral infection ranging from relatively benign warts of the skin or mucous membranes to cancer, the most significant being cervical cancer. Papillomaviruses are known to infect mammals, including humans, rabbits, canines, felines, bovines and equines. Papillomaviruses are highly species and tissue-specific, and are characterized by a specific mode of interaction with the squamous epithelia they infect. These viridae colonize various stratified epithelia like skin and oral and genital mucosae, and induce the formation of self-limited benign tumors, known as warts or condylomas.

An immune response against HPV infection is associated with cell mediated immune function rather than humoral immune function. This function is recognized medically as the basis for this anti-viral activity based on increases in CD4 helper and CD8 killer T cells with respect to combating HPV infection. Biologically, this results from Th-1 cell mediated immune responses with release of cytokines to impart human papilloma virucidal activity. Warts as human papilloma infections can occur in various forms, i.e., common warts (verruca vulgaris), plantar warts (verruca plantaris) & genital warts including venereal and inguinal warts. These are prevalent among all racial groups.

Current therapies as warts treatments are divided into three groups: cellular destruct chemical agents, cryotherapy and immunomodulators. Cellular destructive therapies include chemical agents such as podophyllin, trichloroacetic acid, 5-fluorouracil, bleomycin, retinoids, glutaraldehyde, formaldehyde, salicylic acid and cantharidin. With cryotherapy, a wart is exposed to liquid nitrogen for several treatments spread over three to four weeks required to destruct the warts cellular structure. These treatments results in varying success depending on the nature and severity of the wart lesions. The present invention provides a need in the art for more effective treatments of warts.

Melanoma is a serious form of skin cancer in humans. It arises from the pigment cells (melanocytes), usually in the skin. Melanoma is currently increasing at the fastest rate of all cancers in the United States. Without even including melanoma in-situ, it is the seventh most common serious cancer in the United States.

Melanoma has emerged as the primary model for developing immunotherapies for several reasons. Histopathologic evidence of tumor regression is frequently observed within primary melanoma specimens, along with the presence of tumor infiltrating lymphocytes, thus suggesting a prominent role for the immune system in melanoma (Leong et al., 1996 Surg Clin North Am 76: 1355-81). Melanoma cells readily adapt to tissue culture, resulting in the creation of panels of melanoma cell lines to study. The paucity of effective therapies (chemotherapy, radiation) has resulted in a lower threshold for testing immunological therapies in patients with melanoma (Wolchok et al., 2001 Lancet Oncol II: 205-11; Houghton et al., 2001 Curr Opin Immunol 13: 134-40).

Melanomas are aggressive, frequently metastatic tumors derived from either melanocytes or melanocyte related nevus cells. Melanomas make up approximately three percent of all skin cancers and the worldwide increase in melanoma is unsurpassed by any other neoplasm with the exception of lung cancer in women. Even when melanoma is apparently localized to the skin, up to 30% of the patients will develop systemic metastasis and the majority will die (Kirkwood and Agarwala (1993) Principles and Practice of Oncology 7:1-16).

T cells play an important role in tumor regression in most murine tumor models. Tumor infiltrating lymphocytes (TIL) that recognize unique cancer antigens can be isolated from many murine tumors. The adoptive transfer of these TIL plus interleukin-2 can mediate the regression of established lung and liver metastases (Rosenberg, S. A., et al., (1986) Science 233:1318-1321). In addition, the secretion of IFN-γ by injected TIL significantly correlates with in vivo regression of murine tumors suggesting activation of T-cells by the tumor antigens (Barth, R. J., et al., (1991) J. Exp. Med. 173:647-658). The known ability of tumor TIL to mediate the regression of metastatic cancer in 35 to 40% of melanoma patients when adoptively transferred into patients with metastatic melanoma attests to the clinical importance of the antigens recognized (Rosenberg, S. A., et al., (1988) N Engl J Med 319:1676-1680; Rosenberg S. A. (1992) J. Clin. Oncol. 10:180-199).

Melanomas can metastasize either by the lymphatic or haematogenous route. About two-thirds of metastases are originally confined to the drainage area of regional lymph nodes. A regional metastasis can appear as a micrometastasis in the regional lymph nodes identified via sentinel lymph node biopsy. In contrast to macrometastasis, micrometastasis is not clinically recognizable by palpation or by imaging techniques.

Classic modalities of treating melanoma include surgery, radiation and chemotherapy. For example, standard treatment of a primary tumor is to surgically remove the tumor with adequate margins. However the management of in-transit disease remains extremely challenging. Although surgery may be reasonable when the number of lesions is small, this occurs in only the minority of cases. In the past decade immunotherapy and gene therapy have emerged as new and promising methods for treating melanooma.

Currently, a major treatment for cancerous tumors is surgical removal of the affected areas of the tissue, organ, or gland. However, high recurrence rates are a major obstacle to the complete eradication of cancerous cells. It is believed that although the cancer cells in the malignant tumors can be removed surgically, cancerous cells that have invaded the surrounding tissue or lymph nodes frequently cause tumor recurrence. One reason for frequent tumor recurrence may be that during the development of the primary cancer, complete removal of all the cancer cells by surgical procedures is extremely difficult. Although irradiation, chemotherapy and appropriate hormone therapy all induce apoptosis to some extent in tumor cells, higher doses of the drugs or radiation may be required for suppressing the growth of cancer cells, which, in turn, can cause severe side effects on patients.

Novel strategies are clearly needed to improve the clinical outcome of HPV infection and melanoma. The present invention provides a need in the art for more effective treatments of these diseases.

SUMMARY OF THE INVENTION

The present invention provides a method of treating a disease or disorder associated with human papilloma virus infection in a human patient. The method comprises administering to a first site on the skin of a human patient a low sensitizing dose of an immunomodulating gel composition followed by a subsequent administration to a second site on the skin of the patient a challenge dose of the immunomodulating gel composition, wherein the composition comprises diphenylcyclopropenone (DPCP).

In one embodiment, the disease or disorder associated with human papilloma virus infection is selected from the group consisting of common warts, plantar warts, inguinal warts, venereal warts, and any combination thereof.

In one embodiment, the low sensitizing dose is in the range of about 0.4% DPCP to about 0.6% DPCP, and wherein the challenge dose is in the range of about 0.04% DPCP to about 0.1% DPCP.

In one embodiment, the low sensitizing dose is about 0.4% DPCP, and wherein the challenge dose is about 0.04% DPCP.

In one embodiment, the subsequent challenge dose is administered to the skin of the patient daily.

In one embodiment, the subsequent challenge dose is administered to the skin of the patient every other day.

In one embodiment, the subsequent challenge dose is administered to the skin of the patient biweekly.

In one embodiment, the subsequent challenge dose is administered to the skin of the patient weekly.

In one embodiment, the immunomodulating gel composition further comprises a gel delivery system comprising: a) a first co-solvent comprising a non-ionic surfactant, b) a second co-solvent comprising an alcoholic ester, and c) a gelling agent.

In one embodiment, the first co-solvent is selected from the group consisting of polyoxyethylene (20) monoleate, polyoxyethylene (20) sorbitan monooleate, palmitate and stearate, and wherein the second co-solvent is selected from the group consisting of isopropyl myristate and isopropyl palmitate, and wherein the gelling agent is polyoxyl 40 stearate.

The invention also provides a method of treating cancer in a human patient. The method comprises administering to a first site on the skin of a human patient a low sensitizing dose of an immunomodulating gel composition followed by a subsequent administration to a second site on the skin of the patient a challenge dose of the immunomodulating gel composition, wherein the composition comprises DPCP.

In one embodiment, the cancer is selected from the group consisting of melanoma, cutaneous melanoma, Merkel cell carcinoma, basal cell carcinoma and it's subtype basal cell nevus syndrome, squamous cell carcinoma and it's subtype Bowen's Disease, actinic keratosis, and cutaneous T cell lymphoma and it's subtype mycosis fungoides.

In one embodiment, the low sensitizing dose is in the range of about 0.4% DPCP to about 0.6% DPCPC, and wherein the challenge dose is in the range of about 0.04% DPCP to about 0.1% DPCP.

In one embodiment, the low sensitizing dose is about 0.4% DPCP, and wherein the challenge dose is about 0.04% DPCP.

In one embodiment, the subsequent challenge dose is administered to the skin of the patient daily.

In one embodiment, the subsequent challenge dose is administered to the skin of the patient every other day.

In one embodiment, the subsequent challenge dose is administered to the skin of the patient biweekly.

In one embodiment, the subsequent challenge dose is administered to the skin of the patient weekly.

In one embodiment, the immunomodulating gel composition further comprises a gel delivery system comprising: a) a first co-solvent comprising a non-ionic surfactant, b) a second co-solvent comprising an alcoholic ester, and c) a gelling agent.

In one embodiment, the first co-solvent is selected from the group consisting of polyoxyethylene (20) monoleate, polyoxyethylene (20) sorbitan monooleate, palmitate and stearate, and wherein the second co-solvent is selected from the group consisting of isopropyl myristate and isopropyl palmitate, and wherein the gelling agent is polyoxyl 40 stearate.

The present invention provides a method of treating a disease or disorder associated with human papilloma virus infection in a human patient comprises administering to the skin of the human patient a sensitizing dose of about 0.4% DPCP followed by a challenge dose of about 0.04% DPCP at 14 days and then weekly challenge doses of about 0.04% DPCP for at least 6 weeks.

The present invention provides a method of treating a disease or disorder associated with human papilloma virus infection in a human patient comprising administering to the skin of the human patient a sensitizing dose of about 0.4% DPCP followed by a challenge dose of about 0.04% DPCP at 14 days and then biweekly challenge doses of about 0.04% DPCP for at least 6 weeks.

The present invention provides a method of treating skin cancer in a human patient comprising administering to the skin of the human patient a sensitizing dose of about 0.4% DPCP followed by a challenge dose of DPCP in the range of about 0.04% to about 0.1% at 14 days and then biweekly challenge doses of DPCP in the range of about 0.04% to about 0.1% for a sufficient amount of time.

The present invention provides a method of treating skin cancer in a human patient comprising administering to the skin of the human patient a sensitizing dose of about 0.4% DPCP followed by a challenge dose of about 0.04% DPCP at 14 days and then biweekly challenge doses of about 0.04% DPCP for a sufficient amount of time.

The present invention provides a method of enhancing an immune response in a human patient comprising administering to a first site on the skin of the human patient a low sensitizing dose of an immunomodulating gel composition followed by a subsequent administration to a second site on the skin of the patient a challenge dose of the immunomodulating gel composition, wherein the composition comprises DPCP.

DETAILED DESCRIPTION OF THE INVENTION

The present invention provides a method of sensitizing a subject to a therapeutic modality, comprising administering a sensitizing dose of an immunomodulating gel composition in combination with an effective challenge dose of the immunomodulating gel composition to the subject. Preferably, the immunomodulating gel composition comprises Diphenylcyclopropenone (DPCP). For example, the invention provides a method of sensitizing a subject by administering a sensitizing dose of DPCP at a first site on the subject followed by administration of a challenge dose of DPCP at a second site on the subject.

The present invention is based on the discovery that a low sensitizing dose of about 0.4% DPCP gel compared to the standard sensitizing dose of 2.0% DPCP used in the art prevents the subject from becoming overly hypersensitive to the challenge dose. Sensitizing a subject according to prior art methods at a higher dose of about 2.0% DPCP corresponds to a challenge dose of about 0.002% DPCP because a 2.0% sensitizing dose of DPCP is in essence an "overdose". Thus, prior art sensitizing dose of about 2.0% DPCP results in the subject becoming overly hypersensitive to DPCP and therefore requiring the very low challenge dose of about 0.002% DPCP and in some cases even lower. Contrary to prior art methods, the present invention allows for a higher challenge dose of about 0.04% DPCP compared to the prior art challenge dose of 0.002% DPCP because the relative low sensitizing dose of about 0.4% DPCP compared to 2.0% DPCP does not overly hypersensitize the subject to the challenge dose.

Accordingly, in one embodiment, the present invention relates to a type of topical immunotherapy treatment regimen comprising administering a low sensitizing dose of to a sensitizing site on a subject followed by administration of a treatment dose or otherwise known as a challenge dose of DPCP to a target site on the subject. Preferably, the topical immunotherapy treatment regimen of the invention is useful for the treatment of warts as well as cancer, preferably skin cancer.

In another embodiment, the invention provides a treatment regimen against papilloma virus infection, such as warts (common, plantar and genital warts), using a low dose sensitizing amount of about 0.4% DPCP gel compared to the standard sensitizing dose of 2.0% used in the art in combination with a higher challenge does of about 0.04% DPCP gel compared to the standard challenge dose of 0.002% used in the art. This treatment regimen also provides a therapy against cancer including, but is not limited to melanoma, cutaneous melanoma, Merkel cell carcinoma, basal cell carcinoma and it's subtype basal cell nevus syndrome, squamous cell carcinoma and it's subtype Bowen's Disease, actinic keratosis, and cutaneous T cell lymphoma and it's subtype mycosis fungoides.

The present invention is based on the discovery that a low sensitizing dose of about 0.4% DPCP effectively sensitizes the subject wherein repeated application of a challenge dose of about 0.04% DPCP to the skin enhances the immune response to DPCP. In one embodiment, repeated application of the challenge dose of DPCP enhances production of cytokines from immune cells. In another embodiment, repeated application of the challenge dose of DPCP enhances immune cells to aggregate in the area of application. These immune cells, along with other cells found in the skin, are responsible for the production of anti-viral antibodies and cell-mediated immunity against the agent causing the disease. The immune response induced by the low sensitizing and corresponding challenge dose of DPCP according to the invention is believed to be responsible for the resolution of the disease.

Advantages of the treatment regimen of the invention include the ease of application, relatively low cost, safety, specificity and, most importantly, the painless nature of the treatment. Another advantage is that the relative low sensitizing dose of DPCP of the invention compared to the standard prior art sensitizing dose of 2.0% DPCP allows for a logarithmic increase in the challenge dose compared to the standard challenge dose associated with a sensitizing dose of about 2.0%. Another advantage is that the relative low sensitizing dose of DPCP of the invention allows for more frequent administration of the challenge dose to the subject. For example, the challenge dose can be administered daily, every other day, or biweekly to the subject.

The present invention provides a method of sensitizing a subject to a therapeutic modality, comprising administering a sensitizing dose of immunomodulating gel composition in combination with an effective challenge dose of the immunomodulating gel composition to the subject. Preferably, the immunomodulating gel composition comprises DPCP. For example, the invention provides a method of sensitizing a subject by administering a sensitizing dose of DPCP at a first site on the subject followed by administration of a challenge dose of DPCP at a second site on the subject.

Accordingly, the invention provides a therapy against papilloma virus infection, such as warts (common, plantar and genital warts), using a low dose sensitizing amount of about 0.4% DPCP gel and a challenge does of about 0.04% DPCP gel. The invention also provides a therapy against cancer, preferably skin cancer.

Definitions:

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

As used herein, to "alleviate" a disease means reducing the severity of one or more symptoms of the disease.

The term "apoptosis," as used herein, means an active process, involving the activation of a preexisting cellular pathway, induced by an extracellular or intracellular signal, causing the death of the cell. In particular, the cell death involves nuclear fragmentation, chromatin condensation, and the like, in a cell with an intact membrane.

An "apoptosis-inducing agent" refers to an agent that acts to inhibit cancer-cell proliferation or tumor growth, at least in part, by inducing apoptosis or programmed cell death in cancer cells.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In some instances, hyperproliferative disorders are referred to as a type of cancer including but not limited to primary or metastatic melanoma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

The term "cutaneous lymphoma" refers to tumors essentially consisting of dilated lymph channels of various sizes lined by normal lymph endothelium that may be present only in the skin, but frequently extend into subcutaneous fat and even muscle. The more frequent cutaneous lymphomas are cutaneous T-cell lymphomas and lymphangiomas.

A "disease" is a state of health of an animal wherein the animal cannot maintain homeostasis, and wherein if the disease is not ameliorated, the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"An effective amount" as used herein, means an amount that provides a therapeutic or prophylactic benefit.

The term "enhancing an immune response" means that the method of the invention evokes and/or enhances any response of the animal's immune system, including of either a cell-mediated (i.e. cytotoxic T lymphocyte mediated) or humoral (i.e. antibody mediated) response. These immune responses can be assessed by number of in vitro or in vivo assays well known to those skilled in the art including, but not limited to, cytotoxic T lymphocyte assays, productions of cytokines, regression of tumors, survival of tumor bearing animals, and antibody assays.

The term "fibrosis" relates to and includes the excessive formation or development of fibrous connective tissue in an organ or tissue as a reactive or repairing process, in opposition to the formation of fibrous tissue as a normal constituent of an organ or tissue. Fibrosis includes but is not limited to endomyocardial fibrosis, idiopathic pulmonary fibrosis, emphysema, pulmonary fibrosis (leading to chronic obstructive pulmonary disease), Peyronie's disease, scleroderma, diffuse parenchymal lung disease, cheloids, mediastinal fibrosis, progressive massive fibrosis, proliferative fibrosis, neoplastic fibrosis, renal interstitial fibrosis, hepatic fibrosis, organ fibrosis, surgical scars or burns.

By the term "immune reaction," as used herein, is meant the detectable result of stimulating and/or activating an immune cell.

"Immune response," as the term is used herein, means a process that results in the activation and/or invocation of an effector function in the T cells, B cells, natural killer (NK) cells, and/or antigen-presenting cells (APCs). Thus, an immune response, as would be understood by the skilled artisan, includes, but is not limited to, any detectable antigen-specific or allogeneic activation of a helper T cell or cytotoxic T cell response, production of antibodies, T cell-mediated activation of allergic reactions, and the like.

"Immune cell," as the term is used herein, means any cell involved in the mounting of an immune response. Such cells include, but are not limited to, T cells, B cells, NK cells, antigen-presenting cells (e.g., dendritic cells and macrophages), monocytes, neutrophils, eosinophils, basophils, and the like.

The term "inhibit" is used in reference to a baseline level of a specified activity (e.g., tumor growth or metastasis), which can be the level of the specified activity in the absence of an agent that has the inhibiting activity.

An agent is said to "inhibit the proliferation of cancer cells" if the proliferation of cells in the presence of the agent is less than that observed in the absence of the agent. That is, proliferation of the cells is either slowed or halted in the presence of the agent. Inhibition of cancer-cell proliferation may be evidenced, for example, by reduction in the number of cells or rate of expansion of cells, reduction in tumor mass or the rate of tumor growth, or increase in survival rate of a subject being treated.

The term "Merkel cell carcinoma (MCC)" refers to a neuroendocrine cancer that typically presents as a fast growing unspecific nodule on sun-exposed skin.

By the term "modulating" an immune response, as used herein, is meant mediating a detectable increase or decrease in the level of an immune response in a mammal compared with the level of an immune response in the mammal in the absence of a treatment or compound, and/or compared with the level of an immune response in an otherwise identical but untreated mammal. The term encompasses perturbing and/or affecting a native signal or response thereby mediating a beneficial therapeutic response in a mammal, preferably, a human.

The term "patient" relates to animals, preferably mammals, more preferably human beings, and includes men and women, and children and adults.

The term "sarcomas" refers to tumors of mesodermal origin affecting connective tissue of the skin, subcutaneous tissues or fascial sheaths. The more representative sarcomas affecting the skin are epithelioid cell sarcoma and angiosarcoma.

The term "skin cancer" is used broadly to refer to the malignant proliferation of any cells of the skin. The term "skin cancer" relates to and includes lentigo maligna, melanoma, keratoacanthoma, basal cell carcinoma (BCC), squamous cell carcinoma (SCC), Merkel cell carcinoma (MCC), sarcoma, angiosarcoma, cutaneous lymphoma, sweat gland carcinoma and sebaceous gland carcinoma. Melanoma is a form of skin cancer. In particular, "melanoma" refers to a malignant proliferation of melanocytes. The first phase of most melanomas is termed the radial growth phase (RGP) and is along the dermoepidermal junction and within the dermis. In the vertical growth phase (VGP) growth down through the epidermis brings the malignant melanocytes into contact with lymphatic tissue and capillaries, leading to metastasis.

"Sensitizing" a mammal to an agent, as used herein, refers to the act of enhancing the immune sensitivity of a mammal to an agent.

A "sensitizing effective amount" of the immunomodulating gel composition of the invention means that amount which, when administered to a mammal, especially a human, for treating a disease or condition, is sufficient to sensitize the mammal.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

The term "therapeutically effective amount" refers to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

To "treat" a disease as the term is used herein, means to reduce the frequency of the disease or disorder reducing the frequency with which a symptom of the one or more symptoms disease or disorder is experienced by an animal. The terms "treat", "treating" or "therapeutic", as used herein, also mean a treatment which decreases the likelihood that the subject administered such treatment will manifest symptoms of disease or other conditions.

As used herein, the term "ameliorating" or "treating" means that the clinical signs and/or the symptoms associated with the cancer or melanoma are lessened as a result of the actions performed. The signs or symptoms to be monitored will be characteristic of a particular cancer or melanoma and will be well known to the skilled clinician, as will the methods for monitoring the signs and conditions. For example, the skilled clinician will know that the size or rate of growth of a tumor can monitored using a diagnostic imaging method typically used for the particular tumor (e.g., using ultrasound or magnetic resonance image (MRI) to monitor a tumor).

"Treating a papilloma virus infection" means alleviating or eliminating the symptoms of a papilloma virus infection, or slowing down the progress of a papilloma virus infection.

The term "T-helper" as used herein with reference to cells indicates a sub-group of lymphocytes (a type of white blood cell or leukocyte) including different cell types identifiable by a skilled person. In particular, T-helper cell according to the present disclosure include effector Th cells (such as Th1, Th2 and Th17). These Th cells secrete cytokines, proteins or peptides that stimulate or interact with other leukocytes.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to methods and compositions for sensitizing a mammal, preferably a human, to an immunomodulating gel composition. In this manner, the invention relates to a general method of sensitizing a mammal to an immunomodulating gel composition whereby the subject's immune system is sensitive to a challenge dose of the immunomodulating gel composition. The mammal's sensitive immune response is effective in treating a disease or disorder associated with an inefficient immune response.

In one embodiment, the invention relates to methods and compositions for sensitizing a mammal, preferably a human, to an immunomodulating gel composition for the effective treatment of a papilloma virus infection and skin cancer such as cutaneous metastatic melanoma.

The present invention relates to a type of topical immunotherapy treatment regimen comprising administering a low sensitizing dose of DPCP to a target site followed by administration of a treatment dose or otherwise known as a challenge dose of DPCP to the target site for the treatment of warts as well as skin cancer.

In some instances, administration of the sensitizing dose induces a cutaneous immune response in the mammal prior to the administration of the challenge dose of the DPCP gel to the target site or nearby site. This type of immunotherapy is particularly useful in treating papilloma virus infection including warts or verrucae that are induced by or related to papilloma virus. This type of immunotherapy is also particularly useful in treating epithelial tumors such as cutaneous tumors.

Topical application of a low sensitizing dose of DPCP according to the invention acts by elicitation of sensitivity to a challenge dose at the target site. Preferably, the site of topical application of the initial low sensitizing dose of DPCP is at a different site than the target site for the challenge dose.

In one embodiment, the site for administering the low sensitizing dose of DPCP on a subject is a different site from the target site for which the challenge dose is administered. Preferably, the site for administering the low sensitizing dose is at or around a lymph node. Lymph nodes are distributed throughout the body, with clusters found in the underarms, groin, neck, chest, and abdomen.

A preferred site for administering the low sensitizing dose of DPCP is at or around a lymphatic drainage area. The lymphatic drainage system is organization into two separate and very unequal drainage areas. These are the right and left drainage areas and normally lymph does not drain across the invisible lines that separate these areas. Structures within each area carry lymph to its destination, which is to return to the circulatory system.

The right area drains lymph from the right side of the head and neck, the right arm, and the upper right quadrant of the body. Lymph from this area flows into the right lymphatic duct and this duct empties the lymph into the right subclavian vein.

The left area drains lymph from the left side of the head and neck, the left arm and the left upper quadrant, and the lower trunk and both legs. The cisterna chyli temporarily stores lymph as it moves upward from the lower areas of the body. The thoracic duct transports lymph upward to the left lymphatic duct. The left lymphatic duct empties the lymph into the left subclavian vein.

In one embodiment, a preferred site for administering the low sensitizing dose to the subject is under the inner arm of the subject. In another embodiment, the low sensitizing dose of DPCP can be applied on the forearm of the subject. However, the invention is not limited to the site of administering the low sensitizing dose of DPCP. Rather, the low sensitizing site can be anywhere at or near a lymph node, and preferably at or near a lymphatic drain area.

The low sensitizing dose of about 0.4% DPCP gel according to the present invention results in an unexpected finding from prior art methods. The low sensitizing dose compared to prior art sensitizing doses prevents the subject from becoming overly hypersensitive to the challenge dose. That is, prior art methods employ an initial sensitizing dose of about 2.0% with a corresponding challenge dose of about 0.002%. It is believed that the potency of the challenge dose is inversely proportional to the sensitizing dose. Thus, sensitizing a mammal at a higher dose of about 2.0% corresponds to a challenge dose of about 0.002% because a 2.0% sensitizing dose is in essence an "overdose". Thus, prior art sensitizing dose of about 2.0% results in the subject becoming overly hypersensitive to DPCP and therefore requiring the very low challenge dose of about 0.002% and in some cases even lower.

Routes of administration of the compounds of the invention to a mammal include, but are not limited to, administration by injection, including intravenous, intraperitoneal, intramuscular, and subcutaneous injection, by transmucosal or transdermal delivery, through topical applications, nasal spray, suppository and the like or may be administered orally. The preferred route for the low sensitizing dose and challenge dose of the invention is topical administration.

The topical DPCP gel can be applied by dabbing a cotton-tipped swab that has been saturated with the solution onto the skin or mucous membrane at the desired site of application, without repeated rubbing or spreading the solution over an extended area. For both the sensitization and treatment applications, the topical DPCP gel is preferably left on the skin for a period of time before washing it off. In one embodiment, for both the sensitization and treatment applications, the topical DPCP gel is preferably left on the skin for about 1-72 hours, more preferably 2-60 hours, more preferably 3-48, more preferably 4-36 hours, most preferably 8-24 hours.

In another embodiment, the DPCP gel is applied for both the sensitization and treatment applications with a fixed volume device, such as a micropipette, syringe, or microsyringe. This allows application of a defined volume and therefore a defined amount of the DPCP gel. That can be helpful to produce a more predictable level of intensity of the immune response following application of the DPCP gel. Preferably, the DPCP gel is applied to the target site such as the lesion site without the gel spreading or running to non-target areas.

Composition

In one embodiment, the immunomodulating gel composition of the invention is a unique non-flowable gel composition that is useful for direct topical application of a delayed type contact sensitizer hapten in an anhydrous solubilized drug delivery system. The immunomodulating gel composition of the invention can penetrate the keratinized epithelium of human papilloma virus infections on the skin to reach the antigen presenting cells in the dermis. In this regard, see for example, U.S. Patent Application Publication No. 20060211766 (Kaplan et al.) for immunomodulating gel compositions for treating human papilloma virus infection. The extensive disclosure provided in US20060211766 is incorporated by reference as if set forth in its entirety herein.

In one embodiment, the gel composition comprises 1) a delayed type contact sensitizer hapten; and 2) a gel delivery system. The gel delivery system comprises a first co-solvent comprising a non-ionic surfactant, a second co-solvent comprising an alcoholic ester, and a gelling agent. Preferably, the gel delivery system is anhydrous, non-volatile, and non-irritating. In some instances, the gel delivery system is non-flowable to be retained on the warts surface and the gel is uniquely formulated with surfactants and emollients so as to be able to penetrate the keratinized epithelium of warts surfaces to provide therapeutically effective anti-viral activity.

In one embodiment, the delayed type contact sensitizer hapten is selected from the group consisting of squaric acid dibutylester, diphenylcyclopropenone, dinitrochlorobenzene, dinitrofluorobenzene, exanolone, paraphenylenediamine and urishiol.

In another embodiment, the first co-solvent is selected from the group consisting of polyoxyethylene (20) monoleate, polyoxyethylene (20) sorbitan monooleate palmitate and stearate.

In yet another embodiment, the second co-solvent includes isopropyl myristate or isopropyl palmitate.

In a further embodiment, the gelling agent is polyoxyl 40 stearate.

In one embodiment, the gel composition of the invention comprises diphenylcyclopropenone, butylated hydroxytoluene, polysorbate 80, and isopropyl myristate.

In yet another embodiment, the composition of the invention is useful for the treatment warts. In another embodiment, the composition of the invention is useful for the treatment of neoplastic diseases, such as those diseases caused by melanocytes and melanocytic nevus cells. The invention comprises the administration of an initial low sensitizing dose of about 0.4% DPCP gel at a target site followed by a challenge does of about 0.04% DPCP gel to the target site.

For administration of the composition of the invention, the composition can be suspended in any pharmaceutically acceptable carrier, for example, sterile water or a buffered aqueous carrier, such as glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey), the disclosure of which is incorporated by reference as if set forth in its entirety herein.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as dispersing agents, wetting agents, or suspending agents described herein. Such sterile injectable formulations may be prepared using a non-toxic parenterally-acceptable diluent or solvent, such as water or 1,3-butane dial, for example. Other acceptable diluents and solvents include, but are not limited to, Ringer's solution, isotonic sodium chloride solution, and fixed oils such as synthetic mono- or di-glycerides.

The pharmaceutical compositions described herein can be prepared alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 0.1% to about 10% (w/w) active ingredient, although the concentration of the active ingredient may be as high as the solubility limit of the active ingredient in the solvent. Formulations for topical administration may further comprise one or more of the additional ingredients described herein.

Treatment of Warts

In one embodiment, the present invention relates to methods and compositions for sensitizing mammals, preferably humans, to treat human papilloma virus (HPV) infections. In one embodiment, the invention provides methods and compositions for treating diseases or disorders associated with HPV infection. In some instances, the disease or disorder is caused by HPV Infection.

The methods and compositions described herein can be used to treat diseases and conditions caused by HPV infection, which can be the result of clinical or sub-clinical papillomavirus infections. Such diseases and conditions, herein sometimes called "HPV associated disorders", include but not limited to epithelial malignancies, skin cancer (non-melanoma or melanoma), anogenital malignancies such as cervical cancer, HPV associated precancerous lesions, anal carcinoma, malignant lesions, benign lesions, papillomacarcinomas, papilloadenocystomas, papilloma neuropathicum, papillomatosis, cutaneous and mucosal papillomas, condylomas, fibroblastic tumors, and other pathological conditions associated with papillomavirus.

In some instances, the methods and compositions of the invention described herein can be used to treat warts caused by HPV infection including but not limited to common warts (verruca vulgaris), for example, palmar, plantar, and periungual warts; flat and filiform warts; anal, oral, pharyngeal, laryngeal, and tongue papillomas; and venereal warts (condyloma accuminata), also known as genital warts (for example, penile, vulvar, vaginal and cervical warts), which are one of the most serious manifestations of HPV infection. HPV DNA can be found in all grades of cervical intraepithelial neoplasia (CIN I-III), and a specific subset of HPV types can be found in carcinoma in situ of the cervix. Consequently, women with genital warts, containing specific HPV types, are considered to be at high risk for the development of cervical cancer.

HPV infection has been shown to be associated with cancer. Squamous cell carcinoma has been shown to contain HPV-16 (Baker et al., 1997 Dermatologic Clinics 1997 15: 331-340). Dysplastic periungual papillomas have been shown to have HPV-57. Epidermodysplasia verruciformis is a genetic condition of altered cell-mediated immunity in which affected individuals develop chronic HPV infection and squamous cell carcinoma. There are other states of immunosuppression, both congenital and acquired, that lend to heightened HPV infection and HPV-associated malignancies (Johnson et al., 1999 Consultant 39: 253-266). The risk of malignant transformation may or may not be decreased with treatment. At a minimum, treatment to decrease the spread of HPV may prevent others from developing a cancer promoting infection.

Contrary to prior art methods, the invention is based on the unexpected finding that a low sensitizing dose of about 0.4% DPCP gel allows for a higher challenge dose of about 0.04% DPCP gel. This treatment regimen is an improvement to prior art regimens because the treatment regimen of the invention allows for a higher challenge dose resulting in an effective treatment of papilloma infection, such as warts, having no severe adverse reactions at the application site. In this regard, the treatment regimen of the invention provides a benefit to other prior art regiments because the higher challenge dose of about 0.04% DPCP gel can be tolerated in the subjects sensitized with a low sensitizing dose where otherwise such a higher challenge dose would result in adverse effects when using a relative high sensitizing dose of 2.0% DPCP gel. The treatment regimen of the invention also allows for more frequent challenge dosing of DPCP to the subject.

In one embodiment, the present invention relates to a method of treating a papilloma virus infection in a mammal comprising administering an effective amount of a pharmaceutical composition containing a low sensitizing dose of about 0.4% DPCP gel at a first sensitizing site followed by administering an effective amount of a pharmaceutical composition containing a challenge does of about 0.04% DPCP gel at a second target site.

The treatment regimen of the invention also provides an advantage to prior art regiments because the low sensitizing dose in combination with a higher challenge does allows for desirable clearance rate of warts in a short amount of time. In some instances, the treatment regimen of the invention can clear warts from a subject in about 3 weeks. In other instances, the treatment regimen of the invention can clear warts from a subject in about 4 weeks. In other instances, the treatment regimen of the invention can clear warts from a subject in about 5 weeks. In other instances, the treatment regimen of the invention can clear warts from a subject in about 6 weeks. In other instances, the treatment regimen of the invention can clear warts from a subject in about 7 weeks. In other instances, the treatment regimen of the invention can clear warts from a subject in about 8 weeks. In other instances, the treatment regimen of the invention can clear warts from a subject in about 9 weeks or more.

In one embodiment, the treatment regimen for clearance of warts comprises the initial low sensitizing dose of about 0.04% DPCP gel at the target site and a challenge does approximately 14 days following the initial sensitization and weekly challenge doses of about 0.04% DPCP gel thereafter for various periods. In some instances, the initial challenge dose can be any time after the initial sensitizing dose. For example, the initial challenge dose can be from about 1 through 25 days following the initial sensitizing doses. In another embodiment, the interval of challenge doses can be weekly, biweekly, or every other day. In other embodiments, the days between challenge doses can be 1, 2, 3, 4, 5, 6, 7, 8, 9, 10, 11, 12, 13, 14, 15, 16, 17, 18, 19, 20, or more days.

A suitable low sensitizing dose of DPCP of the invention may be any dose lower than 2.0% DPCP or otherwise the usual sensitizing dose of DPCP currently used in the art. Preferably, the low sensitizing dose of DPCP of the invention is a fraction of about 1-99% of the prior art sensitizing dose of 2.0% DPCP, preferably a fraction of about 10-90% of prior art sensitizing dose of 2.0% DPCP, more preferably a fraction about 20% of prior art sensitizing dose of 2.0% DPCP, yet more preferably a fraction about 25% of prior art sensitizing dose of 2.0% DPCP, yet more preferably a fraction of about 30% of prior art sensitizing dose of 2.0% DPCP, yet more preferably a fraction of about 40% of prior art sensitizing dose of 2.0% DPCP, yet more preferably a fraction of about 50% of prior art sensitizing dose of 2.0% DPCP, yet more preferably a fraction of about 60% of prior art sensitizing dose of 2.0% DPCP, yet more preferably a fraction of about 70% of prior art sensitizing dose of 2.0% DPCP, yet more preferably a fraction of about 80% of prior art sensitizing dose of 2.0% DPCP, yet more preferably a fraction of about 90% of prior art sensitizing dose of 2.0% DPCP.

In one embodiment, the low sensitizing dose of DPCP of the invention is within the range of about 0.01% to about 0.19%, preferably within the range of about 0.2% to about 0.1%, more preferably within the range of about 0.15% to about 0.1%, and more preferably within the range of about 0.2% to about 0.8%, more preferably within the range of about 0.3% to about 0.7%, and most preferably within the range of about 0.4% to about 0.6%. Preferably, the low sensitizing dose of DPCP of the invention is about 0.4% DPCP.

A suitable challenge dose of DPCP may be any dose higher than 0.002% or otherwise the usual challenge dose of DPCP corresponding to the usual sensitizing dose of DPCP used in the art. Preferably, the higher challenge dose of DPCP of the invention is about 1-fold, 2-fold, 3-fold, 4-fold, 5-fold, 6-fold, 7-fold, 8-fold, 9-fold, 10-fold, 20-fold, 100-fold, or more, including any integer in between, of the prior art challenge dose of 0.002%.

In one embodiment, the challenge dose of DPCP is within the range of about 0.002% to about 0.2%, preferably within the range of about 0.01% to about 0.15%, more preferably within the range of about 0.015% to about 0.1%, and more preferably within the range of about 0.02% to about 0.5%, more preferably within the range of about 0.03% to about 0.25%, and most preferably within the range of about 0.04% to about 0.1%. Preferably, the higher challenge dose of DPCP is about 0.04% DPCP.

Treatment of Skin cancer

The present invention relates to immunotherapy of skin cancer, particularly cancers that are induced by infectious agents, particularly viruses, and particularly papilloma viruses.

The present invention also relates to methods and compositions for sensitizing a mammal, preferably a human, to treat a cancer such that a lower dosage of a compound directed against the cancer becomes more effective. Preferably, the cancer is skin cancer. A cancer may belong to any of a group of cancers which have been described elsewhere herein. An example of such a cancer includes, but is not limited to, melanoma, squamous cell carcinoma, basal cell carcinoma, and cutaneous T cell lymphoma.

The invention provides a treatment regimen comprising a low sensitizing dose of about 0.4% DPCP gel followed by a challenge dose of about 0.04% DPCP gel. This treatment regimen is an improvement to prior art regimens because the treatment regimen of the invention allows for a higher challenge dose resulting in an effective reduction of tumor growth having no severe adverse reactions at the application site. In this regard, the treatment regimen of the invention provides a benefit to other prior art regiments because the higher challenge dose of about 0.04% DPCP gel can be tolerated in the subjects sensitized with a low sensitizing dose where otherwise such a higher challenge dose would result in adverse effects when using a relative high sensitizing dose of 2.0% DPCP gel.

The treatment regimen of the invention also provides an advantage to prior art regiments because the low sensitizing dose in combination with a higher challenge does allows for desirable reduction in tumor cell growth in a short amount of time. In some instances, the treatment regimen of the invention can inhibit tumor cell growth from a subject in about 30 weeks. In other instances, the treatment regimen of the invention can inhibit tumor cell growth from a subject in about 40 weeks. In other instances, the treatment regimen of the invention can inhibit tumor cell growth from a subject in about 50 weeks. In other instances, the treatment regimen of the invention can inhibit tumor cell growth from a subject in about 60 weeks. In other instances, the treatment regimen of the invention can inhibit tumor cell growth from a subject in about 70 weeks. In other instances, the treatment regimen of the invention can inhibit tumor cell growth from a subject in about 80 weeks. In other instances, the treatment regimen of the invention can inhibit tumor cell growth from a subject in about 90 weeks or more.

In one embodiment, the treatment regimen for reduction in tumor cell growth comprises the initial low sensitizing dose of about 0.04% DPCP gel at the target site and a challenge does approximately 14 days following the initial sensitization and weekly challenge doses of about 0.04% DPCP gel thereafter for various periods. In some instances, the initial challenge dose can be any time after the initial sensitizing dose. For example, the initial challenge dose can be from about 1 through 25 days following the initial sensitizing doses. In another embodiment, the interval of challenge doses can be daily, every other day, weekly or biweekly. In other embodiments, the days between challenge doses can be 1, 2, 3, 4, 5, 6, 7, 8, 9, 10, 11, 12, 13, 14, 15, 16, 17, 18, 19, 20, or more days.

A suitable low sensitizing dose of DPCP of the invention may be any dose lower than 2.0% DPCP or otherwise the usual sensitizing dose of DPCP currently used in the art. Preferably, the low sensitizing dose of DPCP of the invention is a fraction of about 1-99% of the prior art sensitizing dose of 2.0% DPCP, preferably a fraction of about 10-90% of prior art sensitizing dose of 2.0% DPCP, more preferably a fraction about 20% of prior art sensitizing dose of 2.0% DPCP, yet more preferably a fraction about 25% of prior art sensitizing dose of 2.0% DPCP, yet more preferably a fraction of about 30% of prior art sensitizing dose of 2.0% DPCP, yet more preferably a fraction of about 40% of prior art sensitizing dose of 2.0% DPCP, yet more preferably a fraction of about 50% of prior art sensitizing dose of 2.0% DPCP, yet more preferably a fraction of about 60% of prior art sensitizing dose of 2.0% DPCP, yet more preferably a fraction of about 70% of prior art sensitizing dose of 2.0% DPCP, yet more preferably a fraction of about 80% of prior art sensitizing dose of 2.0% DPCP, yet more preferably a fraction of about 90% of prior art sensitizing dose of 2.0% DPCP.

In one embodiment, the low sensitizing dose of DPCP of the invention is within the range of about 0.01% to about 0.19%, preferably within the range of about 0.2% to about 0.1%, more preferably within the range of about 0.15% to about 0.1%, and more preferably within the range of about 0.2% to about 0.8%, more preferably within the range of about 0.3% to about 0.7%, and most preferably within the range of about 0.4% to about 0.6%. Preferably, the low sensitizing dose of DPCP of the invention is about 0.4% DPCP.

Suitable challenge dose of DPCP may be any dose higher than 0.002% or otherwise the usual challenge dose of DPCP corresponding to the usual sensitizing dose of DPCP used in the art. Preferably, the higher challenge dose of DPCP of the invention is about 1-fold, 2-fold, 3-fold, 4-fold, 5-fold, 6-fold, 7-fold, 8-fold, 9-fold, 10-fold, 20-fold, 100-fold, or more, including any integer in between, of the prior art challenge dose of 0.002%.

In one embodiment, the challenge dose of DPCP is within the range of about 0.002% to about 0.5%, preferably within the range of about 0.01% to about 0.4%, more preferably within the range of about 0.015% to about 0.3%, and more preferably within the range of about 0.02% to about 0.2%, more preferably within the range of about 0.03% to about 0.15%, and most preferably within the range of about 0.04% to about 0.1%.

The frequency of administration of the challenge dose of DPCP can be any frequency that reduces the progression rate of skin cancer without producing significant toxicity to the mammal. For example, the frequency of administration can be from about four times a day to about once every other month, or from about once a day to about once a month, or from about one every other day to about once a week. In addition, the frequency of administration can remain constant or can be variable during the duration of treatment. A course of treatment with the challenge dose can include rest periods. For example, the challenge dose can be administered for five days followed by a nine-day rest period, and such a regimen can be repeated multiple times. As with the effective amount, various factors can influence the actual frequency of administration used for a particular application. For example, the effective amount, duration of treatment, use of multiple treatment agents, and severity of the skin cancer may require an increase or decrease in administration frequency.

An effective duration for administering a composition provided herein can be any duration that reduces the progression rate of skin cancer without producing significant toxicity to the mammal. Thus, the effective duration can vary from several days to several weeks, months, or years. In general, the effective duration for the treatment of skin cancer can range in duration from several days to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the skin cancer.

In some instances, the methods and compositions of the invention described herein can be used to treat cancer, preferably skin cancer. Non-limiting examples of cancers include but are not limited to, melanoma, cutaneous melanoma, Merkel cell carcinoma, basal cell carcinoma and it's subtype basal cell nevus syndrome, squamous cell carcinoma and it's subtype Bowen's Disease, actinic keratosis, and cutaneous T cell lymphoma and it's subtype mycosis fungoides.

The invention also provides compositions and methods of sensitizing a mammal for cancer treatment. For example, the compositions and methods of the present invention can be used in the prevention and treatment of cancer in general or in the treatment of cancer associated with viral replication. For example, the compositions and methods of the invention can be used to treat cutaneous metastatic melanoma.

In one embodiment, the present invention provides methods of inhibiting growth and metastasis of melanoma. In another embodiment, the invention provides methods of sensitizing melanoma cells to apoptosis. In yet another embodiment, the invention provides methods of treating a mammal having melanoma following a treatment regimen comprising administration of a low sensitizing dose of a DPCP gel followed by a challenge does of a DPCP gel to the mammal.

In one embodiment, the invention provides a method for the treatment of melanoma and diseases, in particular neoplastic diseases, caused by melanocytes and melanocytic nevus cells comprising direct topical administration of the DPCP gel on the lesions comprising the cancerous cells. Topical administration may take place directly on the skin, on healthy or normal skin or preferably on, in or around lesions on or in the skin, i.e. on the melanomas or nevi to be treated. The methods of the invention are also applicable to treating pre-melanoma lesions, congenital melanocytic nevi (e.g. Giant Hairy nevus), melanocytic nevi (e.g. atypical or dysplastic nevi), cellular blue nevus and Becker's nevus, all of which are known to be capable of becoming malignant.

Treatment of a melanoma may include the treatment of solid tumors or the treatment of metastasis. Metastasis is a form of cancer wherein the transformed or malignant cells travel and spread the cancer from one site in the body to another. Cancer cells may metastasize through the bloodstream, through the lymphatic system, across body cavities, or any combination thereof. When melanomas have spread to the lymph nodes, micrometastases in which malignancy is only microscopic have a more favorable prognosis than micrometastases. In some cases, micrometastases may only be detected by special staining. If malignancy is only detectable by polymerase chain reaction (PCR), the prognosis is better. Macrometastases in which malignancy is clinically apparent (in some cases cancer completely replaces a node) have a far worse prognosis, and if nodes are matted or if there is extracapsular extension, the prognosis is still worse.

In one aspect, the invention provides a method for inhibiting melanoma growth comprising contacting the melanoma with an effective amount of a first sensitizing dose of DPCP followed by a challenge dose of DPCP. In another aspect, the invention provides a method for inhibiting metastasis of melanoma comprising contacting the melanoma with an effective amount of a first sensitizing dose of DPCP followed by a challenge dose of DPCP. In addition, a method for sensitizing melanoma cells to apoptosis comprising contacting the cells with a first sensitizing dose of DPCP followed by a challenge dose of DPCP is provided.

The current invention is based on the observation that an initial low sensitizing dose of about 0.4% DPCP gel at a target site provides an unexpected therapeutic effect for a challenge dose of about 0.04% DPCP gel. Without wishing to be bound by any particular theory, it is believed that the treatment regimen of the invention comprising a low sensitizing dose followed by a challenge dose serves to induce the immune system to attack the diseased cell. For example, the Langerhans cells, dendritic cells in the skin may be induced by the treatment regimen in a manner that pick up antigens and process them into an 8-mere or 9-mere (or a polypeptide of even 10 to 12 or more aminoacids). As a result, in the regional lymph node this specific polypeptide can subsequently be presented to memory cells within the restrictions of the Major Histocompatibility Complex (MHC). Cytotoxic CD8+ T cells are then generated, which have homing properties, staging the immune response in the original area defined by receptors on endothelial cells of small blood vessels causing the extravasations of these cytotoxic T-cells.

In case of the desired sensitization of the immune system of a melanoma patient following the treatment regimen of the invention, comprising a low sensitizing dose of about 0.4% followed by a challenge dose of about 0.04%, the T-cell mediated cytotoxicity can be directed toward the diseased cells, such as melanocytes. It may be particularly advantageous to repeat the administration to provide a continuous exposure of challenge dose of DPCP to the immune system and thereby boosting the immune response.

In some instances, the repeated challenge doses of DPCP results in a systemic immune reaction against all diseased cells provides an excellent means to combat also distant metastases, even micrometastases, that are not accessible to surgical methods or radiotherapy and which are not accessible for topical drug administration. The capability of melanomas to spread out and to form local and distant metastases is a common problem in treatment of patients suffering from malignant melanomas. This problem can be effectively eliminated with the methods and medicaments of this invention.

The immune response induced in the mammal by administering to the mammal the low sensitizing dose of DPCP following by a challenge dose of DPCP may include cellular immune responses mediated by CD8+ T cells, capable of killing tumor and infected cells, and CD4+ T cell responses. Humoral immune responses, mediated primarily by B cells that produce antibodies following activation by CD4+ T cells, may also be induced. A variety of techniques may be used for analyzing the type of immune responses induced by the compositions of the present invention, which are well described in the art; e.g., Coligan et al., Current Protocols in Immunology, John Wiley & Sons Inc., 1994.

For example, the anticancer activity of the treatment regimen of the invention can be evaluated using standard in vitro and in vivo assays. The ability of a composition to specifically inhibit the growth of tumor cells can be assayed using tumor cell lines in vitro, or in xenograft animal models in vivo. A preferred protocol for such growth curve assays is the short term cell viability assay described in Asai et al. (2003, cited above). In established xenograft models of human tumors, the treatment regimen of the invention is administered either directly to the tumor site or systemically, and the growth of the tumor is followed by physical measurement. A preferred example of a suitable in vivo tumor xenograft assay is also described in Asai et al. (2003, cited above). Other examples are described in Scorski et al., Proc. Natl. Acad. Sci. USA, 94: 3966-3971 (1997) and Damm et al., EMBO J., 20:6958-6968 (2001).

When "an immunologically effective amount," "an anti-tumor effective amount," "a tumor-inhibiting effective amount," or "therapeutic amount" is indicated, the precise amount of the treatment regimen of the present invention to be administered can be determined by a physician with consideration of individual differences in age, weight, tumor size, extent of infection or metastasis, and condition of the patient. It can generally be stated that a pharmaceutical composition comprising the subject cells of the invention, may be administered at a dosage to be determined during appropriate clinical trials. The optimal dosage and treatment regime for a particular patient can readily be determined by one skilled in the art of medicine by monitoring the patient for signs of disease and adjusting the treatment accordingly.

Without wishing to be bound by any particular theory, it is believed that the treatment regimen of the invention activates T helper cells (also known as effector T cells or Th cells), which are a sub-group of lymphocytes (a type of white blood cell or leukocyte) that play an important role in establishing and maximizing the capabilities of the immune, system and in particular in activating and directing other immune cells. Different types of Th cells have been identified that originate in outcome of a differentiation process and are associated with a specific phenotype. Following T cell development, matured, naive (meaning they have never been exposed to the antigen to which they can respond) T cells leave the thymus and begin to spread throughout the body. Naive T cells can differentiate into a T-helper 1 (Th1), T-helper 2 (Th2), T-helper 17 (Th17) or regulatory T cell (Treg) phenotype.

Each of these Th cell types secretes cytokines, proteins or peptides that stimulate or interact with other leukocytes, including Th cells. However, each cell type has a peculiar phenotype and activity that interferes and often conflict with the other.

Th1, Th2, and Th17 (inflammatory T-helper or inflammatory Th), promote inflammation responses trough secretion of pro-inflammatory cytokines, such as IL-1, IL-6, TNF-a, IL-17, IL21, IL23, and/or through activation and/or inhibition of other T cell including other Th cells (for example Th1 cell suppresses Th2 and Th17, Th2 suppresses Th1 and Th17). Tregs instead, are a component of the immune system that suppresses biological activities of other cells associated to an immune response. In particular, Tregs can secrete immunosuppressive cytokines TGF-beta and Interleukin 10, and are known to be able to limit or suppress inflammation.

Th17 cells or otherwise cells exhibiting Th17 cell phenotype may have a variety of specific phenotypic properties, depending on the conditions employed. Such phenotypic properties include production of IL-17A and IFNγ. Moreover, cells activated by the treatment regimen of the invention can produce both IL-17A and IFNγ and help reduce tumor cell growth. It is believed that the cells activated by the treatment regimen of the invention exhibits inflammatory characteristics with an antitumor capacity.

The cytokines that regulate human Th17 cell differentiation have largely been identified (Korn et al., 2009 Annu Rev Immunol 27: 485). IL-1β, IL-6, IL-21, IL-23 and TGFβ play key roles in inducing, expanding and maintaining human Th17 cells (Acosta-Rodriguez et al., 2007 Nat Immunol 8: 942; Wilson et al., 2007 Nat Immunol 8: 950; Yang et al., 2008 Nature 454: 350). Given that Th17 cells are involved in augmenting tumor immunity and in exacerbating multiple autoimmune disorders (Chen et al., 2008 Immunol Res 41: 87; Muranski et al., 2008 Blood 112: 362), it is believed that the treatment regimen of the invention provides a therapeutic benefit to the patient by activating Th17 cells or induce CD4 T helper precursor cells along the Th17 differentiation pathway.

Any method can be used to determine whether or not the progression rate of skin cancer is reduced. For example, the progression rate of skin cancer can be assessed by imaging tissue at different time points and determining the amount of cancer cells present. The amounts of cancer cells determined within tissue at different times can be compared to determine the progression rate. After treatment as described herein, the progression rate can be determined again over another time interval. In some cases, the stage of skin cancer after treatment can be determined and compared to the stage before treatment to determine whether or not the progression rate was reduced.

Combination Therapy with an Immunological Agent

The treatment regimen of the invention can be used in combination with one or more existing immunological agents. The induction of an immune response may be enhanced, accelerated, prolonged by the prior, simultaneous or subsequent use of immune modifying compounds. The purpose of the therapies disclosed herein is to elicit an immune response against certain desired antigens, which elicitation may be enhanced by administering compounds capable of activating or stimulating immune responses. Such compounds may include various adjuvants and immune modifiers known in the art. In one embodiment, the use of compounds or compositions that are able to recruit lymphocytes to the site of the lesion, to activate professional antigen presenting cells (such as dendritic cells or langerhans cells), may be combined with the treatment regimen of the invention. For instance Toll like receptor (TLR) activating compounds and/or adjuvants such as LPS, lipid A, peptidoglycans, flagellins, dsRNA, ssRNA, CpG DNA, Pam3Cys or immunemodifyers such as imiquimod or resiquimod, CD40 ligands or activating antibodies may be systemically, but preferably topically, applied to stimulate a local inflammatory response in the lesion treated according to the invention. Adjuvants may also be advantageously used in combination with the invention. Furthermore, compounds such as cytokines (interleukins), chemokines and interferons that stimulate, enhance or prolong an immune response can be used in combination with the treatment regimen of the invention. This can be done by providing them directly or by stimulating their local synthesis or release. Particularly the use of interferon gamma and interleukins may be used to stimulate the generation of a cellular and humoral immune response against the desired antigen, in particular by recruitment and activation of professional antigen presenting cells.

For use in treating a mammal with cancer such as skin cancer, in accordance with the present invention, the cancer must be one that responds to an immunological agent directed against a target cancer-cell antigen. Examples of immunological agents, and associated cancers which are targets for the agent, include agents whose immunological moiety is designed for targeting CD19 and CD20, for treating of B-lineage leukemias, such as chronic lymphoblastic leukemia (CLL) and non-Hodgkin-lymphomas (NHL), agents targeting CD22, for treating hairy cell leukemias, agents targeting CD25, CD7, CD64, and CD33, for treating various haematological malignancies expressing CD25, CD7, CD64, or CD33, respectively, agents targeting MCSP, for treating malignant melanomas, agents targeting a Lewis Y Antigen, for treating adenocarcinomas, and agents targeting IL13 or EGFR, for treating a variety of tumors known to express these antigens, such as glioblastomas.

Thus, an aspect of the invention involves identifying cancer patients who are candidates for effective anti-cancer treatment with an immunological agent, but for whom combined treatment with the treatment regimen of the invention is desired to enhance the anti-tumor efficacy of the immunological agent.

In the preferred treatment method, the subject is administered the immunological agent in an amount that is effective inhibiting proliferation of cancer cells in the subject. The dose administered and the dosing schedule will follow, for example, known or recommended doses for antibody agents currently in use for anti-tumor therapy, such as Rituximab, as indicated, for example, in the drug product insert or published clinical or animal-model data. One advantage of the present invention is that lower-than-normal doses of the immunological agent can be administered, if necessary, due to the compensating enhancement effect of the treatment regimen of the invention. Thus, a kit containing a dose of the immunological agent could optionally contain a product insert having one set of directions for using the agent in monotherapy, and another set of directions for using DPCP in a combination therapy to sensitize the subject. The set of instructions for the combination therapy could recommend a lower dose of the immunological agent, when used in combination with the treatment regimen of the invention, and/or a different dosing regimen for one or both agents, when used together, than would normally be recommended for the immunological agent when used alone.

The treatment regimen of the invention may be administered, before, during, or after administration of the immunological agent. Typically, the immunological agent and DPCP are administered in a common dosing regimen, and the two compounds themselves may be administered in a combined-drug composition. However, a dosing regimen in which the sensitizing and challenge dose of DPCP of the invention is administered before or after administering the immunological agent is also contemplated. For example, a subject under treatment with an immunological agent may be subsequently placed on a combined therapy that includes the treatment regimen of the invention.

Alternatively, the subject may be initially administered with the treatment regimen of the invention comprising a low sensitizing dose of DPCP and a challenge dose of DPCP followed by the administration of the immunological agent at a later time. In this type of treatment schedule, the low and high doses of DPCP serves, in part, to sensitize the cancer cells towards responding to the immunological agent.

The immunological agent may be administered by direct injection of a tumor or its vasculature. Alternatively, the tumor may be infused or perfused with the agents using any suitable delivery vehicle. The agents may be administered locally to an affected organ. Systemic administration may also be performed. Continuous administration may be applied where appropriate; for example, where a tumor is excised and the tumor bed is treated to eliminate residual disease. Delivery via syringe or catheterization is preferred. Such continuous perfusion may take place for a period from about 1-6 hours, to about 6-12 hours, to about 12-24 hours, to about 1-2 days, to about 1-2 weeks or longer following the initiation of treatment. Generally, the dose of the therapeutic composition via continuous perfusion will be equivalent to that given by a single or multiple injections, adjusted over a period of time during which the perfusion occurs.

The immunologic agent can be administered to a subject, such as a human patient, in a formulation and in an amount effective to achieve a clinically desirable result. For the treatment of cancer, desirable results include reduction in tumor mass (as determined by palpation or imaging; e.g., by radiography, radionucleotide scan, CAT scan, or MRI), reduction in the rate of tumor growth, reduction in the rate of metastasis formation (as determined e.g., by histochemical analysis of biopsy specimens), reduction in biochemical markers (including general markers such as ESR, and tumor specific markers such as serum PSA), and improvement in quality of life (as determined by clinical assessment, e.g., Karnofsky score), increased time to progression, disease-free survival and overall survival.

In another embodiment, the treatment regimen of the present invention can be combined with the use of Nitrogen mustard (mechlorethamine) in the treatment of cancer. Nitrogen Mustard is a chemotherapy drug that is normally given intravenously to treat the entire body. When mixed in an ointment, it is a useful treatment for lymphomas of the skin. In this regard, see for example, U.S. Patent Application Publication No. 20100041767 for compositions and methods of treating cancer comprising Nitrogen Mustard. The extensive disclosure provided in US20100041767 is incorporated by reference as if set forth in its entirety herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: Low Dose Sensitization of DPCP for the Treatment of Warts

Patients were initially sensitized with 0.4% DPCP gel at the primary wart site. Approximately 14 days later and weekly thereafter for various periods, a challenge dose is then applied. A challenge dose of 0.04% DPCP was employed. The DPCP used was incorporated in a unique blend of surfactants, a viscosity agent, and a preservative. See Table 1 and 2.

TABLE 1

0.4% DPCP sensitizing dose

| | % | 1000 gram batch |
|---|---|---|
| Diphenylcyclopropenone | 0.40 | 4.0 |
| Butylated hydroxytoluene NF | 0.02 | 0.2 |
| Polysorbate 80 NF | 49.79 | 497.9 |
| Isopropyl myristate NF | 49.79 | 497.9 |

TABLE 2

0.04% DPCP challenge dose

| | % | 1000 gram batch |
|---|---|---|
| Diphenylcyclopropenone | 0.040 | 0.40 |
| Butylated hydroxytoluene NF | 0.01 | 0.10 |
| Polysorbate 80 NF | 49.975 | 499.75 |
| Isopropyl myristate NF | 49.975 | 499.75 |

It was observed that the treatment regimen of 0.4% DPCP sensitizing dose in combination with a challenge dose of 0.04% DPCP exhibited at least two benefits. First, the treatment regimen using a low sensitizing dose of 0.04% DPCP avoided unnecessary adverse events compared to a treatment regimen using a 2.0% DPCP sensitizing dose. Without wishing to be bound by any particular theory, it is believed that subjects using a 2.0% DPCP sensitizing dose develop a severe reaction at the site of administration including minor blistering and weeping. The present treatment regimen avoids this severe reaction.

The second benefit of the treatment regimen is derived from the challenge dose. Without wishing to be bound by any particular theory, it is believed that potency of the challenge dose needs to be inversely proportional to the sensitizing dose. The starting challenge dose typically employed when started at 2.0% DPCP is 0.002% DPCP. It is believed that a 2.0% DPCP sensitizing dose is in essence an "overdose" and the subject becomes hypersensitive to DPCP and therefore requires the very low challenge dose of 0.002% and in some cases even lower (e.g., 0.001%). In contrast to the 2.0% DPCP sensitization dose treatment regimen, the current treatment regimen employing a challenge dose of 0.04% DPCP did not result in observable severe reactions at the application site. In this regard, the current treatment regimen provides a benefit to other regiments because the 0.04% DPCP challenge dose has been tolerated so well in the subjects tested. Accordingly, another study was conducted which applied the 0.4% DPCP sensitizing dose on Day 0 and starting on Day 14 application of the 0.04% DPCP challenge dose twice weekly for seven more weeks. The present study has demonstrated an excellent wart clearance rate with just 6 weekly challenge doses. Without wishing to be bound by any particular theory, it is believed that 7 weeks of biweekly treatment will produce excellent wart clearance rates.

Experiments were designed to determine the efficacy and safety of administering DPCP at a low dose 0.4% sensitizing and a 0.04% therapy dose for the treatment of warts.

The materials and methods employed in the experiments disclosed herein are now described.

Study Design and Outcomes

Institutional review board approval was obtained for this study, which was performed using Good Clinical Practice Guidelines and was compliant with the Code of Federal Regulation of the US Food and Drug Administration. A single center, randomized, double-blind, placebo control study using low dose DPCP in a non-volatile vehicle for the treatment of non-genital warts was conducted. Patients were assigned to a treatment or placebo group in a 2:1 fashion. The two study gels were identical in appearance. The treatment group was sensitized with 0.1 ml of 0.4% DPCP gel which was applied to the inner arm and washed off in 24 hours. Fourteen days after the sensitization dose, 0.1 ml of 0.04% DPCP gel was applied to each wart, up to a total of 4 warts, for 7 consecutive weeks (Day 14, 21, 28, 35, 42, 49, 56). A final follow-up examination was performed on day 70. Patients were assessed at baseline and during each of 7 week treatment visits and on day 70 follow up.

Efficacy was based on Lesion Surface Area. The size of each qualifying verruca wart was determined at each visit by measuring the longest dimension (long axis) and the corresponding widest dimension (90 to the long axis).

Investigator's Global Assessment Score (IGAS) was calculated based upon the following 4 point scale: 3 points Complete clearance; 2 points=partial clearance: >50% reduction in the area of all treated wart; 1 point=partial eradication: <50% reduction in the area of all treated warts; 0 points=treatment failure: complete or partial eradication not achieved.

Immunotherapeutic responses were characterized by grading the erythema, edema, induration, and scaling on a four-point scale: 0 (none) to 4 severe at each visit.

Efficacy endpoints were determined based on the percent of patients achieving complete and partial eradication as measured by IGAS and reductions in warts lesion surface area. Subjects were assessed for the extent of their immunotherapeutic response to treatment based upon the degree of erythema, edema, induration and scaling. Safety was evaluated at each visit by recording and grading adverse events and ease of ambulation 4 point grading system was used.

Study Population

Adults 18-75 years of age in general good health with at least one non-genital cutaneous wart 5-20 mm in size were eligible for participation in the study. Women of child bearing potential (WOCBP) had a negative pregnancy test at baseline visit and were to use highly effective contraception throughout the study. Pregnant or nursing women were excluded. Patients with unstable medical condition or history of immunosuppression were excluded. Use of systemic steroids, immunosuppressants, immunomodulators or cimetidine was not allowed for 4 weeks prior to enrollment. Any prior wart therapy was not allowed for 4 weeks. Patients could not have significant scarring or active dermatologic condition in the treatment area. Patients could not be actively enrolled in another clinical trial within the previous 30 days.

The results of the experiments disclosed herein are now described.

A total of 18 subjects with non-genital warts were enrolled and randomized in the study (11 female and 7 males). A total of 17 subjects completed day 14 for sensitization results and 14 patients completed the study. Four subjects withdrew during the study for personal reasons.

A total of 8 subjects (25 total warts) in the DPCP group and 6 subjects (15 warts) in the vehicle group completed the study. The age range was 19-79 years old.

Sensitization reactions developed in 9 of 12 (75%) of subjects who received 0.4% DPCP gel and 0 of 6 (0%) subjects who received vehicle developed a sensitization reaction, Chi-square 9.0, p=0.0027.

All subjects (100%) in the DPCP group obtained a clinical response/improvement. Partial to complete clearance occurred in 19/25 (76%) warts and of the 6 warts that did not respond, 4 of 6 (67%) were in subjects who did not elicit a sensitization reaction.

Complete clearance occurred in 11 of 25 warts (44%) in the DPCP group and 1 of 15 (6.7%) of vehicle treated warts, Chi-square 6.22, p=0.01

One subject with numerous mosaic warts on the plantar foot in the DPCP group had 4 warts treated and achieved complete clearance of those 4 warts and all surrounding untreated warts (>50).

No significant side effects were reported other than skin rash at the sensitization site. Patients reported both treatments to be highly tolerable.

The results presented herein demonstrate that using a lower dose of a sensitizer such as 0.4% DPCP gel as compared to prior art sensitizing dose of about 2.0% DPCP is safer since the low dose sensitizer of about 0.4% DPCP decreases potential adverse reaction. The sensitizing dose of about 0.4% DPCP in combination with a challenge dose of about 0.04% DPCP is effective at eliciting an immune reaction and is more effective than the control group at successfully clearing warts.

Example 2: Low Dose Sensitization of DPCP for the Treatment of Verruca Conditions Institutional review board approval was obtained for this study, which was performed using Good Clinical Practice Guidelines and was compliant with the Code of Federal Regulation of the US Food and Drug Administration. A single center, 24 subject, randomized, double-blind, placebo control study using low dose DPCP in a non-volatile vehicle for the treatment of non-genital warts of established.

Patients are assigned to a treatment or placebo group in a 2:1 fashion. The two study gels are identical in appearance. Both groups are sensitized with 0.1 ml of 0.4% DPCP gel which is applied to the inner arm and washed off in 24 hours. Fourteen days after the sensitization dose, 0.1 ml of 0.04% DPCP gel or placebo is applied to each wart, up to a total of 4 warts, twice a week for 7 consecutive weeks (Day 14, 21, 28, 35, 42, 49, 56, 63). A final follow-up examination is performed on day 77. Patients are assessed at baseline and during office visits on days 14, 28, and 63 and on the day 77 follow up visit.

Efficacy is based on Lesion Surface Area. The size of each qualifying verruca wart is determined at each visit by measuring the longest dimension (long axis) and the corresponding widest dimension (90 to the long axis).

Investigator's Global Assessment Score (IGAS) is calculated based upon the following 4 point scale: 3 points=Complete clearance; 2 points=partial clearance: >50% reduction in the area of all treated wart; 1 point=partial eradication: <50% reduction in the area of all treated warts; 0 points=treatment failure: complete or partial eradication not achieved.

Immunotherapeutic responses are characterized by grading the erythema, edema, induration, and scaling on a four-point scale: 0 (none) to 4 severe at each visit.

Efficacy endpoints are determined based on the percent of patients achieving complete and partial eradication as measured by IGAS and reductions in warts lesion surface area. Subjects are assessed for the extent of their immunotherapeutic response to treatment based upon the degree of erythema, edema, induration and scaling. Safety is evaluated at each visit by recording and grading adverse events and ease of ambulation 4 point grading system is used.

The materials and methods employed in the experiments disclosed herein are now described.

Study Design

Day 0—First Office Visit

All subjects (both treated and placebo groups) are sensitized with the initial sensitizing dose of 0.4% DPCP gel applied directly to one target wart and to the inner aspect of the right arm and then covered with an occlusive adhesive bandage pad for 24 hours.

Day 14—Second Office Visit

The Investigator can determine if sensitization occurred at either of the application sites. If on day 14, the first "treatment visit", no visible evidence of skin sensitization is observed then the subject can be dropped from the study. If on day 14 the investigator determines that sensitization has occurred, than the first treatment dose using the challenge dose (0.04% DPCP gel or placebo) randomly assigned upon enrollment can be administered by the investigator to all target warts and then covered with an occlusive adhesive bandage pad for 24 hours.

The patient is provided with a tube containing the appropriate challenge product (0.04% DPCP gel or placebo) with detailed instructions on how to apply the product two times per week and the proper handling and storage of the product between applications.

Treatment Weeks 1, 2, and 3—Days 18, 21, 25

Two times per week the patient can apply the treatment dose (0.04% DPCP gel or placebo) to all target warts and then cover with an occlusive adhesive bandage pad for 24 hours. The patient is instructed to omit an application to any target wart(s) that exhibit an excess of inflammation and to resume applications when the inflammation has subsided.

Treatment Day 28—Office Visit 3

Efficacy for each target lesion is graded and any adverse reactions can be reviewed, recorded, and treated as deemed medically necessary. Photographs of warts taken are compared with initial photographs from the sensitization visit.

The Investigator can apply the treatment dose (0.04% DPCP gel or placebo) to all target warts and then cover with an occlusive adhesive bandage pad for 24 hours. The Investigator can omit an application to any target wart(s) that exhibit an excess of inflammation and the patient is instructed to resume applications when the inflammation has subsided.

Treatment Weeks 3, 4, 5, and 6—Days 31, 35, and 38 45, 49, 52, 56, 59

Two times per week the patient can apply the treatment dose (0.04% DPCP gel or placebo) to all target warts and then cover with an occlusive adhesive bandage pad for 24 hours. The patient is instructed to omit an application to any target wart(s) that exhibit an excess of inflammation and to resume applications when the inflammation has subsided.

Treatment Day 63—Office Visit 4

Efficacy for each target lesion is graded and any adverse reactions can be reviewed, recorded, and treated as deemed medically necessary. Photographs of warts taken are compared with initial photographs from the sensitization visit.

The Investigator can apply the treatment dose (0.04% DPCP gel or placebo) to all target warts and then cover with an occlusive adhesive bandage pad for 24 hours. The Investigator can omit an application to any target warts) that exhibit an excess of inflammation. This is the final treatment. The patient is instructed to stop at home treatments and should return any unused gel.

Day 77—Office Visit 5—Follow Up Visit

Efficacy for each target lesion is graded and any adverse reactions can be reviewed, recorded, and treated as deemed medically necessary. Photographs of warts taken are compared with initial photographs from the sensitization visit.

Study Population

Adults 18-75 years of age in general good health with at least one non-genital cutaneous wart 5-20 mm in size are eligible for participation in the study. HIV+ patients with CD4+ cell counts greater than 300 are also eligible. Women of child bearing potential (WOCBP) had a negative pregnancy test at baseline visit and are to use highly effective contraception throughout the study. Pregnant or nursing women are excluded. Patients with unstable medical condition are excluded. Use of systemic steroids, immunosuppressants, immunomodulators or cimitidine is not allowed for 4 weeks prior to enrollment. Any prior wart therapy is not allowed for 4 weeks. Patients could not have significant scarring or active dermatologic condition in the treatment area. Patients could not be actively enrolled in another clinical trial within the previous 30 days.

The results of the experiments disclosed herein are now described.

To date a total of 7 subjects have been enrolled and randomized in the study. A total of 5 subjects (6 total warts) in the DPCP group and 2 subjects (3 warts) in the vehicle group have completed the study.

In this study both the treatment group and the placebo group received a 0.4% DPCP sensitization dose and all were successfully sensitized.

4/5 subjects (80%) in the DPCP group obtained a clinical response/improvement. Complete clearance occurred in 4/6 (67%) of the treated warts and 1/6 (16%) achieved greater than 50% clearance and 1/6 (16%) exhibited no clearance. No partial or complete clearance occurred in the 3 warts treated in the placebo group. See Table 3.

TABLE 3

| Subject # | Wart Location | Treatment | Clearance Score |
|---|---|---|---|
| 107 | 0.5 mm rt hand | DPC | 7 weeks + 3 |
| 108 | 0.5 mm left arm | DPC | 5 weeks + 3 |
| 109 | 0.5 mm left finger | Placebo | 5 weeks 0 |
| 109 | 0.2 mm | Placebo | 5 weeks 0 |
| 110 | 0.9 mm left hand | DPC | 7 weeks + 3 |
| 110 | 0.5 mm | DPC | 7 weeks + 2 |
| 111 | 0.5 mm left hand | Placebo | No show for treatment |
| 112 | 0.5 mm left finger | DPC | 7 weeks 0 |
| 113 | 0.6 mm rt.finger | Placebo | Patient withdrew after 5 weeks |
| 114 | 0.4 mm rt.finger | DPC | 7 weeks + 3 |

No significant side effects were reported other than skin rash at the sensitization site. Patients reported both treatments to be highly tolerable.

The results presented herein demonstrate that using a lower dose of a sensitizer such as 0.4% DPCP gel as compared to prior art sensitizing dose of about 2.0% DPCP is safer since the low dose sensitizer of about 0.4% DPCP decreases potential adverse reaction. The sensitizing dose of about 0.4% DPCP in combination with a challenge dose of about 0.04% DPCP applied topically twice a week for seven weeks is effective at eliciting an immune reaction and is more effective than the control group at successfully clearing warts, Chi-square 7, p=0.01. The results presented herein demonstrate that using a lower dose of a sensitizer such as 0.4% DPCP gel compared to the standard sensitizing dose of 2.0% is safer since the lower dose sensitizer of the invention decreases potential adverse reaction.

Without wishing to be bound by any particular theory, it is believed that the challenge dose can be applied every other day or even more frequently.

Example 3: Low Dose Sensitization of DPCP for the Treatment of Cutaneous Metastatic Melanoma Patients are initially sensitized with 0.4% DPCP gel by way of topical administration at the target site. Approximately 14 days later and weekly thereafter for various periods, a challenge dose is then applied. A challenge dose of 0.04% DPCP is employed. The DPCP used was incorporated in a unique blend of surfactants, a viscosity agent, and a preservative. See Table 1 and 2.

Without wishing to be bound by any particular theory, the treatment regimen using a low sensitized dose of 0.4% DPCP allows for a greater range of challenge doses and frequency of about 0.04% DPCP. This treatment regimen can be an effective treatment of many types of skin cancer, including but not limited to basal cell carcinoma, actinic keratosis, Bowen's disease, squamous cell carcinoma, cutaneous melanoma and the like.

A patient exhibiting symptoms of skin cancer or precancerous skin conditions would receive an initial low sensitizing dose of 0.4% DPCP with challenge doses starting at 0.04%. In some instances, the challenge dose can be increased to a desirable amount such as up to 0.2% DPCP. The frequency of application of the challenge dose can start at twice a week. In some instances, the frequency of the challenge does can be increased to three or four times a week.

Depending on the type of skin cancer (for example squamous cell carcinoma and cutaneous melanoma), it may be desirable to start with a sensitizing dose of 0.4% DPCP with challenge doses starting at 0.04% but possibly increasing up to 0.5% and even up to 2.0%. The ability to increase the challenge dose is based on the discovery that the low sensitization dose allows for having the challenge dose be higher than otherwise possible if the sensitizing dose was higher than 0.4% DPCP. The low sensitizing dose allows for a higher challenge dose having less adverse reactions compared to the adverse reactions using a sensitizing that is higher than 0.4% DPCP. The frequency of the challenge does can start at twice a week and if needed be increased to daily use.

Example 4: Employing the Topical Immunomodulator Diphenylcyclopropenone in a Stabilized Gel to Treat In-Transit Metastases in Cutaneous Melanoma The following experiments were designed to conduct a Phase II open-label study to determine the dose response and safety and efficacy of DPCP incorporated in a unique blend (see Table 1 and 2) as a topical immunotherapy for the treatment of cutaneuos melanoma. It is believed that the DPCP incorporated in a unique blend provides a new topical immune based therapy which provides an effective, low cost, safe, easy to use, noninvasive therapy for the treatment of in-transit metastases in cutaneous melanoma.

The primary purpose of this study is to test the safety of multiple applications of the treatment formulation. The study also anticipates an indication of the effectives of the DPCP formulation to treat cutaneous melanoma in-transit metastases.

The materials and methods employed in the experiments disclosed herein are now described.

Phase IIa Clinical Study

The present study is an open-label study to determine the response and characteristics, safety and efficacy, of the DPCP gel composition as a topical immunotherapeutic agent for the treatment of in-transit metastases in cutaneous melanoma. The products evaluated include 0.4% DPCP, in a non-volatile gel vehicle as the initial treatment topically applied in a single dose and 0.04% DPCP in the same gel vehicle applied to the target lesions biweekly for 14 weeks. The estimated duration of the study is 142 days with 112 days of treatment followed by subject examination on day 142.

The study population includes male or female subjects, aged 18 years or older with in-transit cutaneous melanoma metastases. Inclusion criteria are as follows:

Male or non-pregnant female subjects aged 18-75 years of age.

Written and verbal informed consent must be obtained.

Subjects with clinically diagnosed cutaneous melanoma with multiple in-transit metastases. Investigator must determine that the subject's metastatic lesions are not candidates for excision or other approved treatments.

Women of childbearing potential (WOCBP) must be willing to practice effective contraception for the duration of the study.

WOCBP must have a negative urine pregnancy test at the baseline visit.

Subjects must be willing and able to have the therapy applied by the investigator, must be willing and able to apply the therapy to themselves and must be willing and able to comply with study instructions and return to the clinic for required visits.

Exclusion criteria include the following:

Subjects taking any of the following systemic or topical therapies within 4 weeks of enrollment: cimetidine, corticosteroids, or immunosuppressants, and/or any other medicines that may affect the outcome of this study.

Subjects who have active localized or systemic medical conditions that in the opinion of the investigator, would preclude their participation in the study.

Subjects with any underlying disease(s) or dermatological condition of the affected area(s) that requires the use of interfering topical or systemic therapy.

Subjects who are pregnant, nursing mothers, subjects planning a pregnancy during the course of the study.

Subjects who are unable to communicate or cooperate with the Investigator due to language problems, poor mental development, or impaired cerebral function Subjects with any condition, which, in the Investigator's opinion, would make it unsafe for the subject to participate in a research study.

Subjects who have been treated with another investigation device or drug within 30 days prior to study enrollment.

Justification of Biopsies

The study includes a histological standard skin biopsy at Day 0, Day 35, and the final treatment visit, Day 112. These biopsies help to confirm the presence of viable melanoma at the target site before, during, and at the end of the treatment period. Additional tests can be performed on the biopsy tissue to determine the level of immune system activity at the target site. CD8, Natural Killer cells, TH17 cells, and cytokine levels are measured to determine the level of immune system activity.

Justification of the Sample Size

DPCP has an extensive history of previous human use but it has never been subjected to the full clinical development process required for regulatory approval in the United States. Up to this point DPCP formulations have been prepared as required in small lab-scale batches using acetone as the vehicle. This study employs a vehicle that avoids both the handling and skin damaging drawbacks of employing acetone as the vehicle. The study also uses a much lower sensitization concentration of 0.4% DPCP versus the usually employed 2.0% sensitization concentration.

Study Procedures

Day 0—First Office Visit:

Sensitization visit: Following signed written Informed Consent and confirmation of eligibility, all subjects undergo a medical history including review of concomitant medications, and a dermatologic exam is performed to confirm the presence of eligible in-transit cutaneous melanoma metastases. A pregnancy test is administered in WOCBP and must be negative in order for the subject to participate in the trial. A standard skin punch biopsy can be performed to confirm viable melanoma at the target site. Photographs of the target lesions can be taken and the initial sensitizing dose can be applied directly to one target lesion and to the inner aspect of the right arm. The sensitizing sites can then be covered with an occlusive adhesive bandage pad for 24 hours.

Day 14—Second Office Visit

The Investigator can determine if sensitization occurred at either of the application sites. If on day 14, the first "treatment visit", no visible evidence of skin sensitization is observed then an additional sensitization dose of 0.4% DPCP can be applied to the target lesions and covered for 24 hours. The patient is instructed to return in one week.

At the discretion of the treating physician, a 0.4% DPCP dose can be administered at any office visit if the melanoma medications are insufficiently inflamed or not responding to the lower 0.04% DPCP take home product.

If on day 14, the investigator determines that sensitization has occurred, than the first treatment dose using the challenge dose of 0.04% DPCP gel can be administered by the investigator to all target lesions. The lesions are then covered with an occlusive adhesive bandage pad for 24 hours. The patient can be be provided with a tube containing the challenge dose 0.04% DPCP gel with detailed instructions on how to apply the product two times per week and the proper handling and storage of the product between applications.

Days: 17, 21, 24, 28, 31—Treatment Doses #3 thru 7

The challenge dose of 0.04% DPCP can be administered by the subject to all target lesions and then covered with an occlusive adhesive bandage pad for 24 hours. In the event one or more target lesion(s) has a delayed type hypersensitivity (DTH) reaction of 4+ (e.g., large vesicles, bullae, and severe local reaction besides erythema), the investigator/subject may elect to not perform a scheduled treatment on the target lesion(s). The treatment schedule is resumed when the inflammation subsides. During this period any adverse reactions should be immediately reported to the Principal Investigator by the subject.

Patient Visit 3—Treatment #8—Day 35

Prior to the treatment regimen, a photograph of the target lesions can be taken in order to grade the lesions. A standard skin punch biopsy can be used to confirm viable melanoma at the target site. Additional tests can be performed on the biopsy tissue to determine the level of an immune response at the target site. CD8 T cells, Natural Killer cells, TH17 cells, and cytokine levels can be measured using standard assays to evaluate the level of immune response at the target side.

The challenge dose of 0.04% DPCP can then be administered by the Investigator to all target lesions and covered with an occlusive adhesive bandage pad for 24 hours. In the event one or more target lesion(s) has a DTH reaction of 4+ (e.g., large vesicles, bullae, and severe local reaction besides erythema), the investigator/subject may elect to not perform a scheduled treatment on the target lesion(s). The treatment schedule is resumed when the inflammation subsides. Any adverse reactions should be recorded during this visit.

Days: 38, 42, 45, 59, 63, 66, 70, 73, 77, 80—Treatment doses #s 9 thru 20

The challenge dose of 0.04% DPCP can be administered by the subject to all target lesions. The lesions are then covered with an occlusive adhesive bandage pad for 24 hours. In the event one or more target lesion(s) has a DTH reaction of 4+ (e.g., large vesicles, bullae, and severe local reaction besides erythema), the investigator/subject may elect to not perform a scheduled treatment on the target lesion(s). The treatment schedule is resumed when the inflammation subsides. During this period any adverse reactions should be immediately reported to the Principal Investigator by the subject.

Patient Visit 4—Treatment #21-Day 80

Prior to the treatment regimen, a photograph of the target lesions can be taken in order to grade the lesions. The challenge dose of 0.04% DPCP can then be administered by the Investigator to all target lesions and covered with an occlusive adhesive bandage pad for 24 hours. In the event that one or more target lesion(s) has a DTH reaction of 4+ (e.g., large vesicles, bullae, and severe local reaction besides erythema), the investigator/subject may elect to not perform a scheduled treatment on the target lesion(s). The treatment schedule is resumed when the inflammation subsides. Any adverse reactions should be recorded during this visit.

Days: 84, 87, 91, 94, 98, 101, 105, 108—Treatment doses #s 22 thru 29

The challenge dose of 0.04% DPCP can be administered by the subject to all target lesions. The lesions are then covered with an occlusive adhesive bandage pad for 24 hours. In the event that one or more target lesion(s) has a DTH reaction of 4+(e.g., large vesicles, bullae, and severe local reaction besides erythema), the investigator/subject may elect to not perform a scheduled treatment on the target lesion(s). The treatment schedule is resumed when the inflammation subsides. During this period any adverse reactions should be immediately reported to the Principal Investigator by the subject.

Patient Visit 5—Treatment #30—Day 112

Prior to treatment with a challenge dose of DPCP, a photography of the target lesions can be taken for purposes of grading the lesions. A standard skin punch biopsy can be performed to confirm viable melanoma at the target site. Additional tests can be performed on the biopsy tissue to determine the level of immune system activity at the target site. CD8 T cells, Natural Killer cells, TH17 cells, and cytokine levels can be measured using standard assays in the art.

The challenge dose of 0.04% DPCP can then be administered by the Investigator to all target lesions and covered with an occlusive adhesive bandage pad for 24 hours. In the event one or more target lesion(s) has a DTH reaction of 4+ (e.g., large vesicles, bullae, and severe local reaction besides erythema), the investigator/subject may elect to not perform a scheduled treatment on the target lesion(s). The treatment schedule is resumed when the inflammation subsides. Any adverse reactions should be recorded during this visit.

Patient Visit 6—Follow up Visit—Day 142

Final photographs of the target lesions are taken and the target lesions are graded. The resolution or occurrence of any adverse reactions should be recorded during this visit.

Without wishing to be bound by any particular theory, it is believed that the risks of the present study are minimal. The most common adverse effects of DPCP are a mild contact dermatitis/eczema similar to poison ivy reaction, along with lymph node swelling. Less common adverse effects are localized blistering, hyperpigmentation, and eczema at a distant site from the application site. Rare adverse effects are fever and chills, fainting spells, flu-like symptoms, headache, palpitation, and rarely contact leukoderma, erythema multiforme and urticaria. DPCP has demonstrated that it is not mutagenic, teratogenic and has no organ toxicity.

Potential risks of the medication is minimized by the study through the use of a much lower sensitization concentration of 0.4% DPCP versus the usually employed 2.0% sensitization concentration along with the use the gelled DPCP composition of the present invention that avoids the handling and skin damaging drawbacks of the standard DPCP in acetone. Potential risk is also minimized by utilizing trained physicians to closely monitor for any adverse reaction, to withdrawal the subject if medically indicated and to refer for treatment as deemed medically necessary. If a severe blister reaction occurs which is a possible but uncommon reaction of DPCP, cold wet compresses or even hydrocortisone cream or pill, can be used.

Study Measurements

Efficacy of the treatment regimen can be assessed by the following:

Lesion Surface Area: the size of each qualifying melanoma lesion is determined at each evaluation by measuring the longest dimension (long axis) and the corresponding widest dimension (90 to the long axis).

Investigator's Global Assessment Score (IGAS) is evaluated for all treated lesions as a group based upon the following 4 point scale: 3 points—complete eradication (e.g., elimination of all treated lesions and restoration of normal epidermal lines and marking; 2 points—(partial eradication: >50% reduction in the area of all treated lesions); 1 point—(partial eradication: <50% reduction in the area of all treated lesions); 0 points—(treatment failure: complete or partial eradication not achieved).

Immunotherapeutic responses are characterized by grading the erythema, edema, induration, and scaling on a four-point scale, 0 (none) to 4 severe at each visit.

Study Endpoints

Efficacy Endpoints can be determined based on the percent of patients achieving complete and partial eradication, reductions in Lesion Surface Area as well as the IGAS, over the treatment period and on the follow up visit on day 142. Histological presence of melanoma at the biopsy sites at the beginning and the end of the treatment period can be confirmed. During the post-treatment period efficacy measurements, test subject acceptance, and reported adverse reactions can be evaluated.

Subjects are assessed for the extent of their immunotherapeutic response to treatment based upon the degree of erythema, edema, induration and scaling. CD8 T cells, Natural Killer cells, TH17 cells, and cytokine level measurements are evaluated to determine immune response to the treatment.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of treating skin cancer in a human patient, the method comprising administering to a first site on the skin of a human patient a sensitizing immunomodulating gel composition comprising from about 0.2% (w/w) to about 0.8% (w/w) diphenylcyclopropenone (DPCP), and subsequently administering to a second site on the skin of said patient a challenge immunomodulating gel composition comprising from about 0.01% (w/w) to about 0.4% (w/w) DPCP, wherein said skin cancer in the human patient is treated.

2. The method of claim 1, wherein said cancer is selected from the group consisting of melanoma, cutaneous melanoma, Merkel cell carcinoma, basal cell carcinoma, squamous cell carcinoma, actinic keratosis, and cutaneous T cell lymphoma.

3. The method of claim 1, wherein said sensitizing immunomodulating gel composition comprises from about 0.4% (w/w) DPCP to about 0.6% (w/w) DPCP, and wherein said challenge immunomodulating gel composition comprises about 0.04% (w/w) DPCP to about 0.1% (w/w) DPCP.

4. The method of claim 1, wherein said sensitizing immunomodulating gel composition comprises about 0.4% (w/w) DPCP, and wherein said challenge immunomodulating gel composition comprises about 0.04% (w/w) DPCP.

5. The method of claim 1, wherein a subsequent challenge dose is administered to the skin of said patient daily.

6. The method of claim 1, wherein a subsequent challenge dose is administered to the skin of said patient every other day.

7. The method of claim 1, wherein a subsequent challenge dose is administered to the skin of said patient biweekly.

8. The method of claim 1, wherein a subsequent challenge dose is administered to the skin of said patient weekly.

9. The method of claim 1, wherein said immunomodulating gel composition further comprises a gel delivery system comprising a first co-solvent comprising a non-ionic surfactant, a second co-solvent comprising an alcoholic ester, and a gelling agent.

10. The method of claim 9, wherein said first co-solvent is selected from the group consisting of polyoxyethylene (20) monoleate, polyoxyethylene (20) sorbitan monooleate, palmitate and stearate, and wherein said second co-solvent is selected from the group consisting of isopropyl myristate and isopropyl palmitate, and wherein said gelling agent is polyoxyl 40 stearate.

11. A method of treating skin cancer in a human patient, the method comprising administering to the skin of a human patient a sensitizing immunomodulating gel composition comprising about 0.4% (w/w) DPCP, and subsequently administering to the skin of the patient a challenge immunomodulating gel composition comprising DPCP in the range of about 0.04% (w/w) to about 0.1% (w/w) at 14 days and then biweekly administering to the skin of the patient a challenge immunomodulating gel composition comprising DPCP in the range of about 0.04% (w/w) to about 0.1% (w/w) for a sufficient amount of time.

12. A method of treating skin cancer in a human patient, the method comprising administering to the skin of a human patient a sensitizing immunomodulating gel composition comprising about 0.4% (w/w) DPCP, and subsequently administering to the skin of the patient a challenge immunomodulating gel composition comprising about 0.04% (w/w) DPCP at 14 days and then biweekly administering to the skin of the patient a challenge immunomodulating gel composition comprising about 0.04% (w/w) DPCP for a sufficient amount of time.

* * * * *